(12) United States Patent
Yamagishi et al.

(10) Patent No.: US 8,352,416 B2
(45) Date of Patent: Jan. 8, 2013

(54) DIAGNOSTIC REPORT SEARCH SUPPORTING APPARATUS AND DIAGNOSTIC REPORT SEARCHING APPARATUS

(75) Inventors: Hiromasa Yamagishi, Otawara (JP); Hikaru Futami, Otawara (JP); Kenichi Niwa, Otawara (JP)

(73) Assignees: Kabushiki Kaisha Toshiba, Tokyo (JP); Toshiba Medical Systems Corporation, Otawara-shi (JP)

( * ) Notice: Subject to any disclaimer, the term of this patent is extended or adjusted under 35 U.S.C. 154(b) by 239 days.

(21) Appl. No.: 12/821,617

(22) Filed: Jun. 23, 2010

(65) Prior Publication Data

US 2011/0004595 A1   Jan. 6, 2011

(30) Foreign Application Priority Data

Jul. 2, 2009   (JP) .................................. 2009-157983
May 20, 2010  (JP) .................................. 2010-115906

(51) Int. Cl.
   *G06F 7/00* (2006.01)
(52) U.S. Cl. ...................................................... 707/602
(58) Field of Classification Search ................... 707/602
   See application file for complete search history.

(56) References Cited

U.S. PATENT DOCUMENTS

| | | | |
|---|---|---|---|
| 2001/0044720 A1* | 11/2001 | Lee et al. | 704/251 |
| 2007/0237375 A1 | 10/2007 | Yamagishi et al. | |
| 2009/0132499 A1 | 5/2009 | Yamagishi et al. | |
| 2009/0192824 A1 | 7/2009 | Minakuchi et al. | |

FOREIGN PATENT DOCUMENTS

JP   2007-293521   11/2007

* cited by examiner

*Primary Examiner* — Truong Vo
(74) *Attorney, Agent, or Firm* — Oblon, Spivak, McClelland, Maier & Neustadt, L.L.P.

(57) ABSTRACT

According to embodiments, a diagnostic report search supporting apparatus and a diagnostic report searching apparatus each have a report registering part, a structuring processing part, a related-term analyzing part, a counting part, and a keyword extracting part. The structuring processing part extracts terms from a sentence written in a diagnostic report, and classifies the terms into predetermined kinds. The related-term analyzing part generates combinations each composed of two or more terms based on the plurality of terms having been extracted. The counting part counts the existence number of same combinations in the plurality of combinations, and extracts combinations whose existence numbers are a predetermined number or more. The keyword extracting part extracts a combination including a desired keyword, and extracts a term other than the desired keyword as a related keyword.

10 Claims, 28 Drawing Sheets

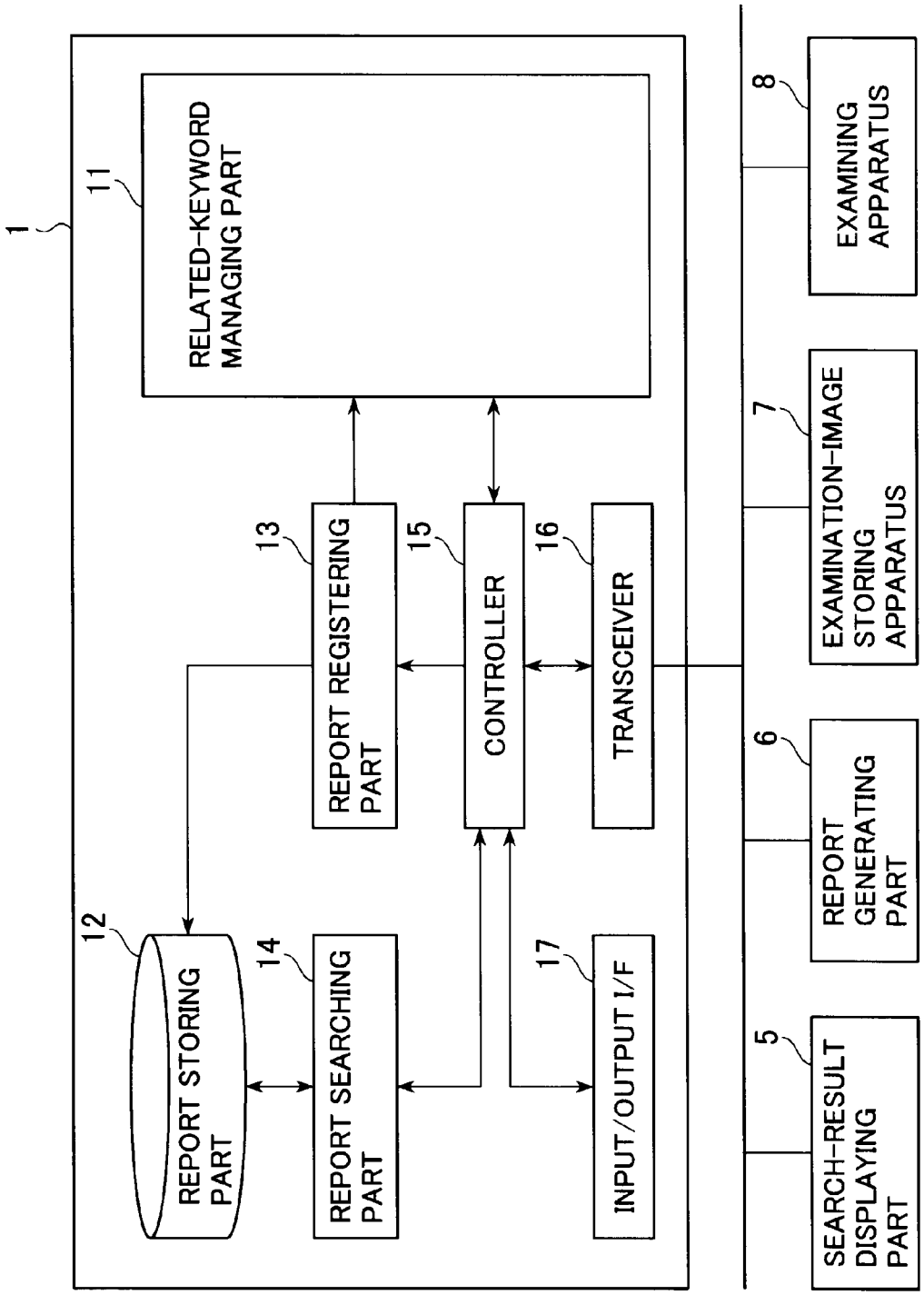

FIG.2

| REPORT ID |
| PATIENT NAME |
| EXAMINATION DATE |

FINDING FIELD

. . . . . . . . . . . . . . . . . . . . . . . .

GROUND-GLASS OPACITY IS SEEN IN LEFT LUNG FIELD.
  wm        wj      wu        wb

. . . . . . . . . . . . . . . . . . . . .
. . . . . . . . . . . . . . . . . . . . .

⎬ Cs

DIAGNOSED-DISEASE-NAME FIELD

LUNG ADENOCARCINOMA ～wd

| SEMANTIC UNIT | | EXISTENCE NUMBER |
|---|---|---|
| LEFT LUNG FIELD — OPACITY | | 100 |
| LEFT LUNG FIELD — GROUND-GLASS | | 100 |
| OPACITY — GROUND-GLASS | | 50 |
| LUNG ADENOCARCINOMA — LEFT LUNG FIELD | | 50 |
| LUNG ADENOCARCINOMA — OPACITY | | 200 |
| LUNG ADENOCARCINOMA — GROUND-GLASS | | 50 |
| ...... | | ... |

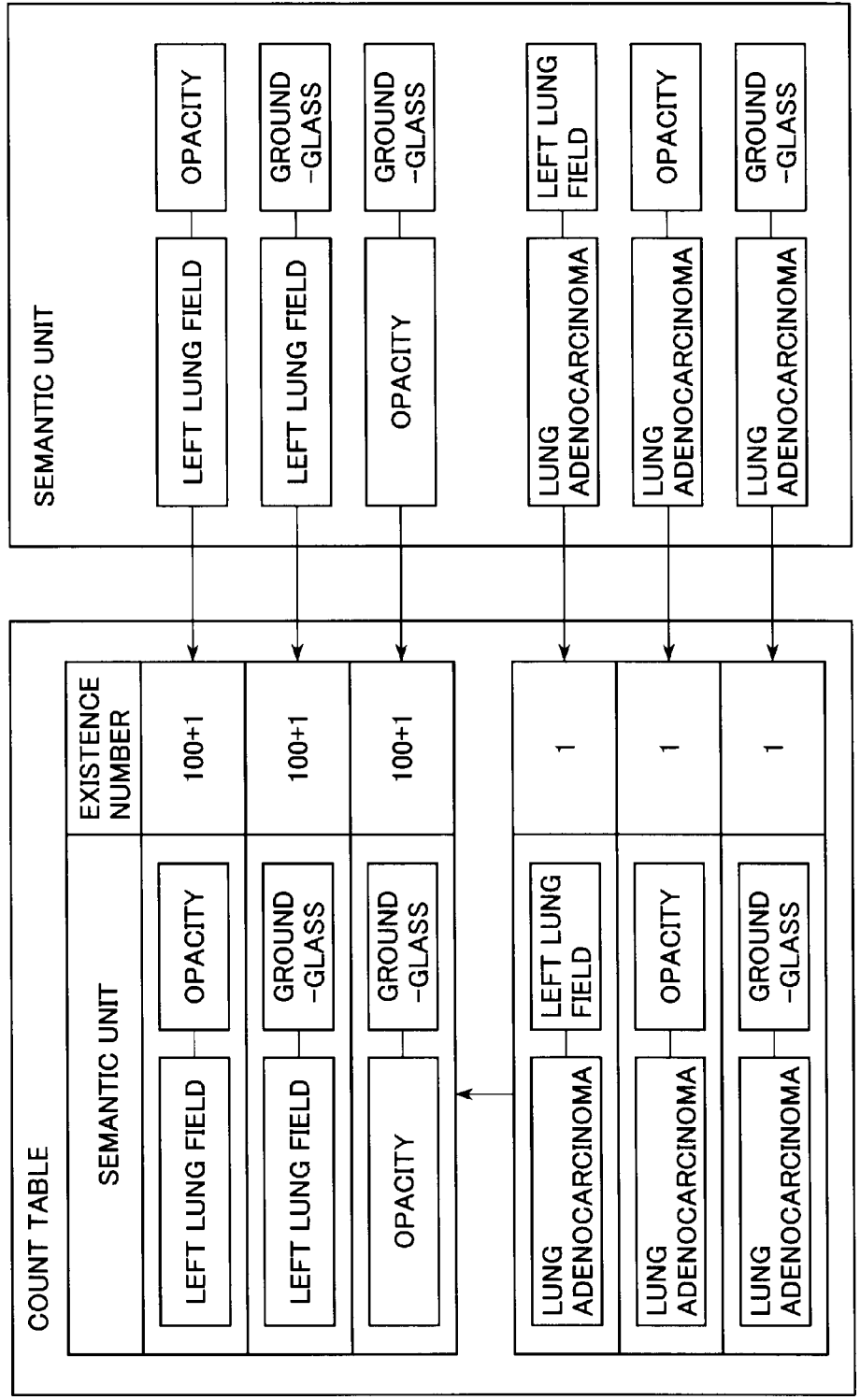

FIG.8

KEYWORD INPUT FIELD

| LUNG FIELD, LUNG TUMOR |

RELATION SELECTION

- ☑ INCLUSION RELATION
- ☑ SIMILARITY RELATION
- ☑ AFFECTED REGION AND CASE NAME
- ☑ FINDING
- ☑ SEARCH HISTORY

KEYWORD-EXTRACTION-RESULT DISPLAY

☑ LUNG FIELD                                                                 [ SEARCH ]

| | | |
|---|---|---|
| INCLUSION | ☐ UPPER LOBE | ☐ LOWER LOBE |
| SIMILARITY | ☐ LUNG (JAPANESE) | ☐ LUNG (ENGLISH) |
| REGION /CASE | ☐ LUNG CANCER | ☑ SQUAMOUS CELL CANCER |
| FINDING | ☑ OPACITY | ☐ GROUND-GLASS    ☐ ··· |
| HISTORY | ☑ HEART HYPERTROPHY | ☑ PLEURAL    ☐ ··· |

☑ LUNG TUMOR

| | | |
|---|---|---|
| INCLUSION | ☐ ADENOCARCINOMA | ☐ SQUAMOUS CELL CANCER |
| SIMILARITY | ☑ LUNG CA | ☑ LUNG CANCER |
| REGION /CASE | ☐ S3 | ☐ LUNG |
| FINDING | ☐ OPACITY | ☑ GROUND-GLASS    ☐ ··· |
| HISTORY | ☐ OBSOLETE TUBERCULOSIS | ☑ LUNG METASTASIS    ☐ ··· |

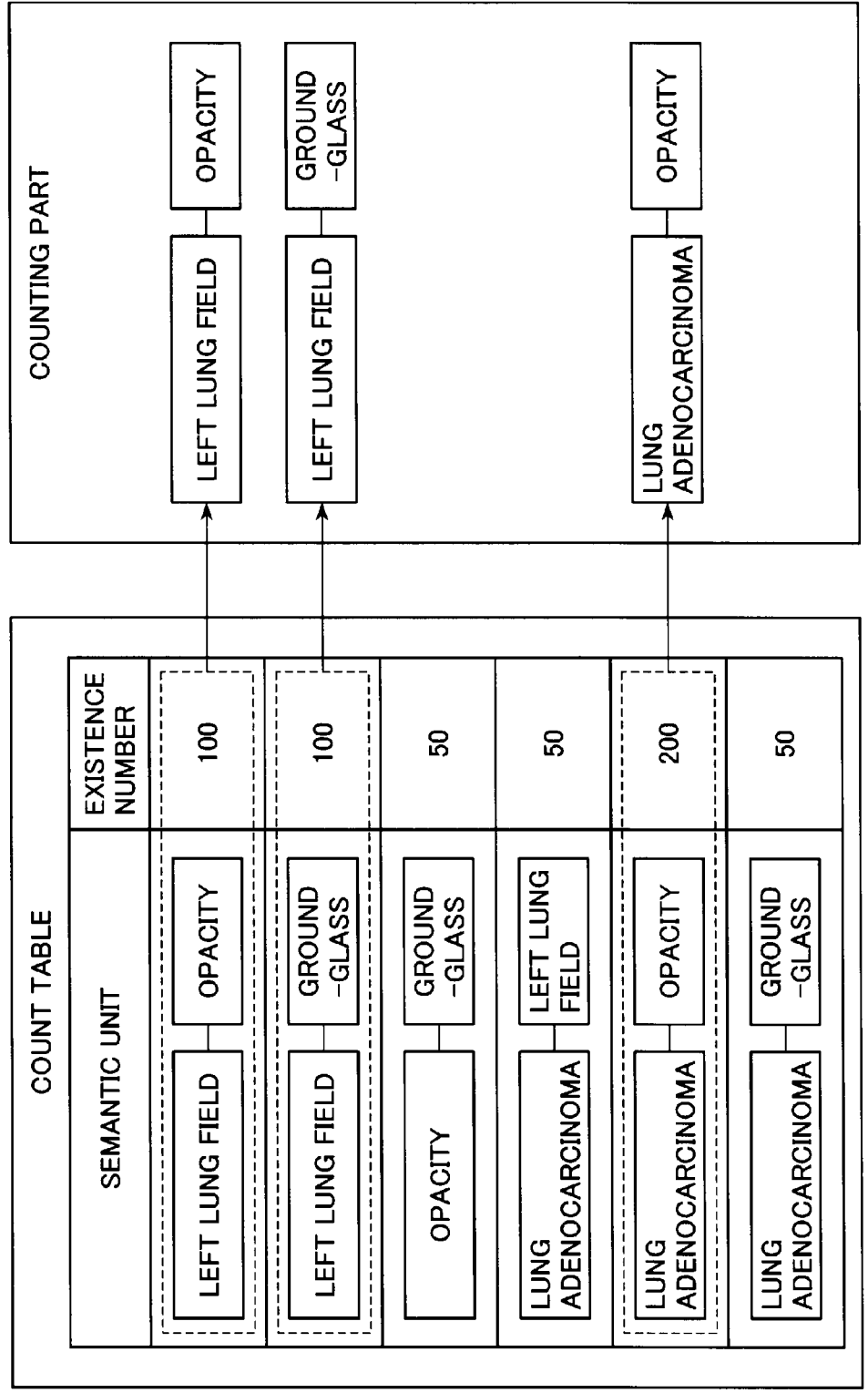

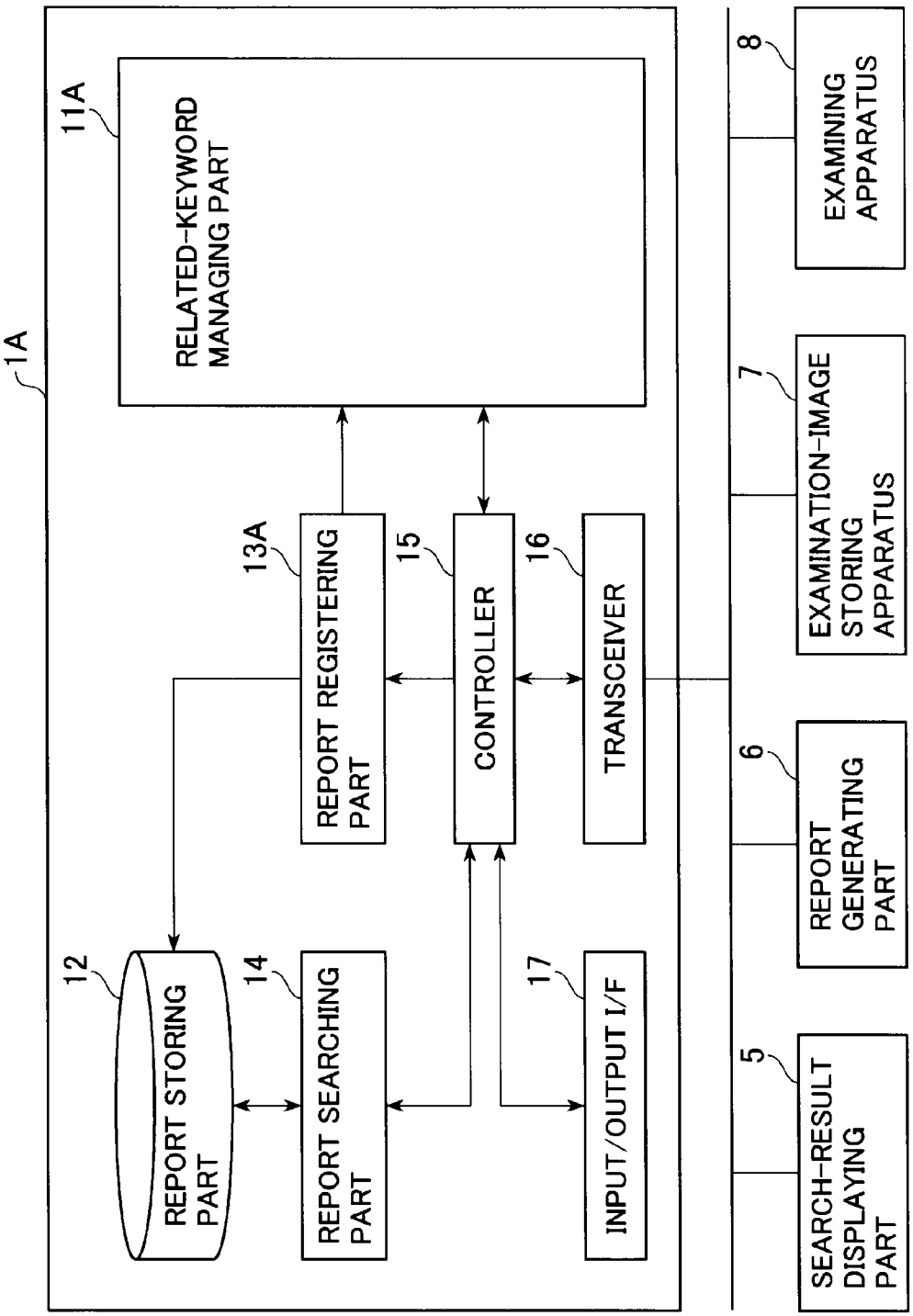

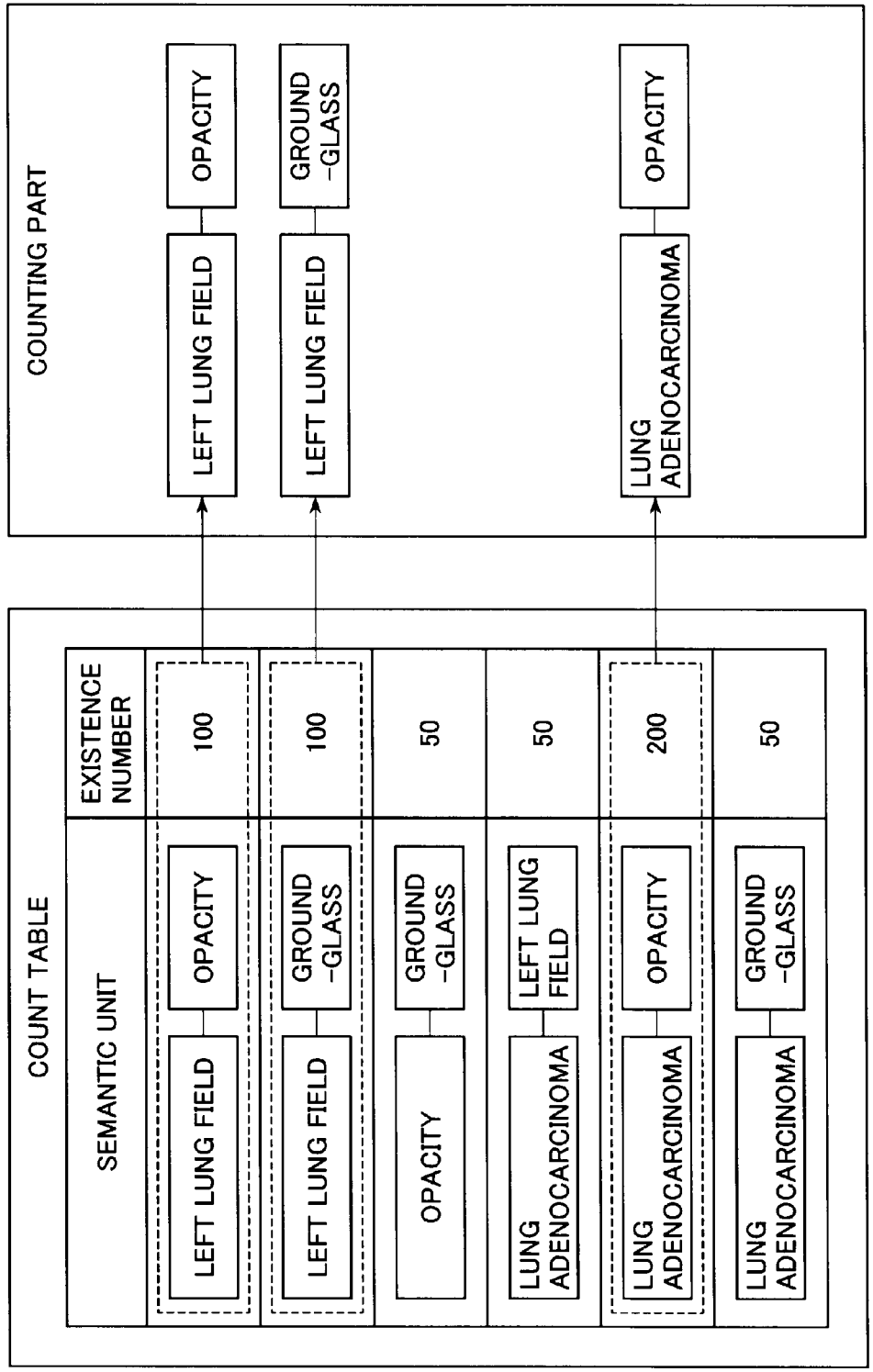

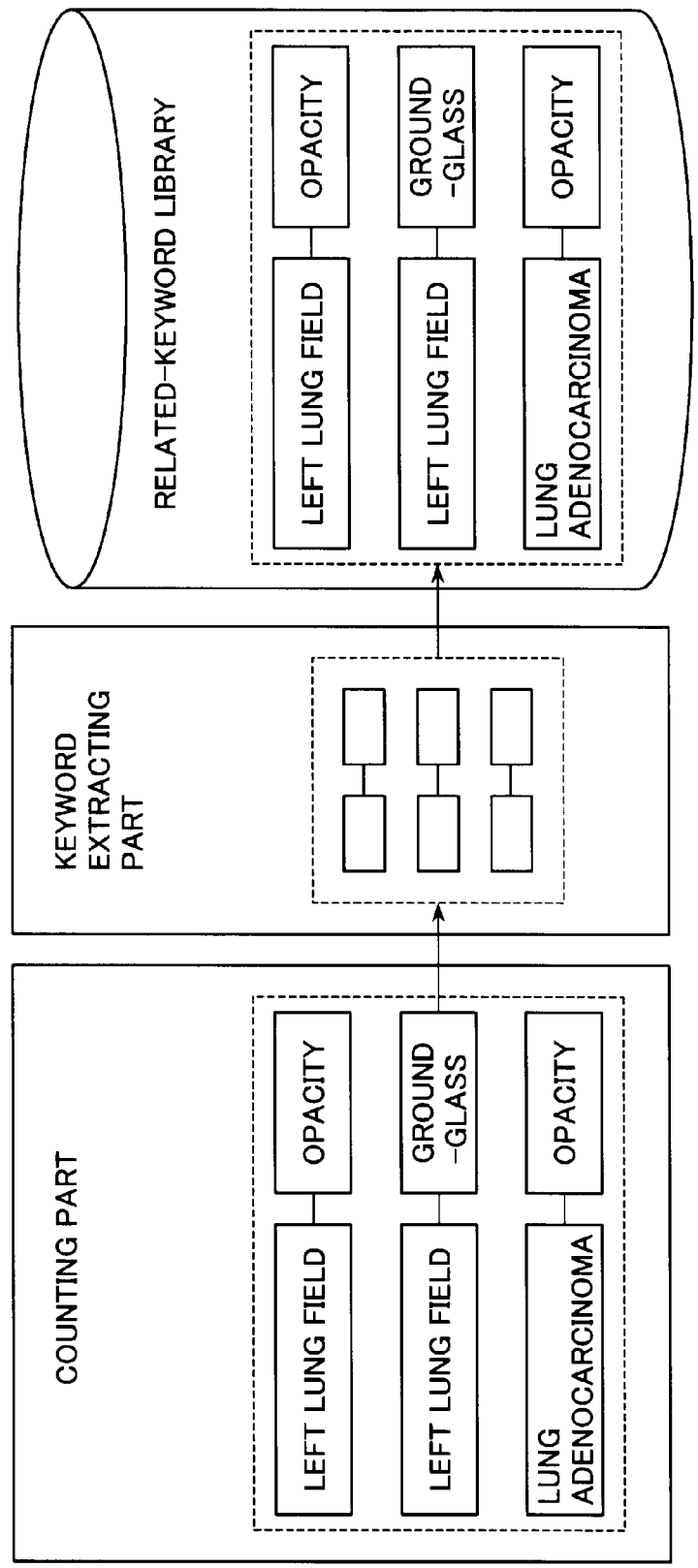

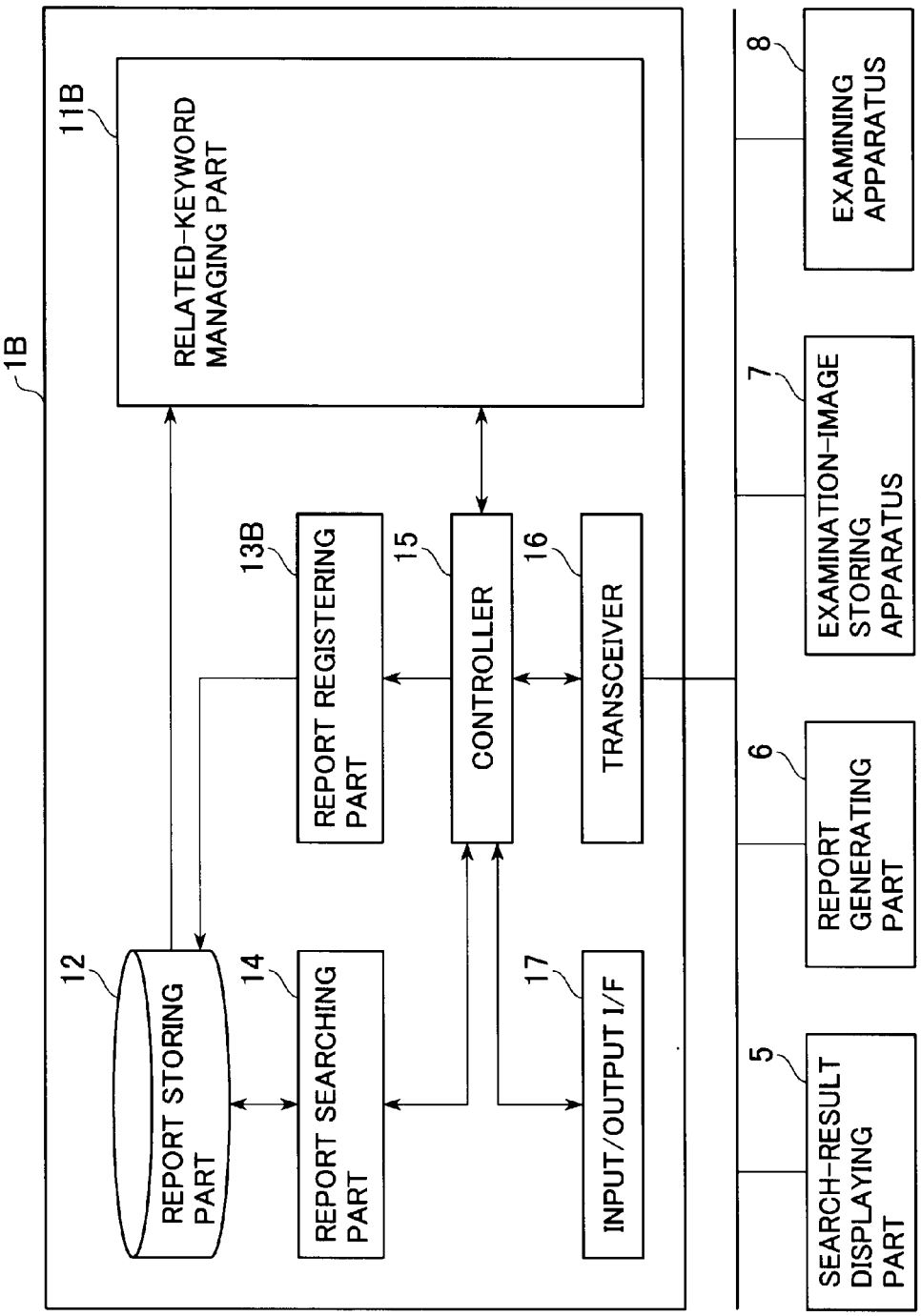

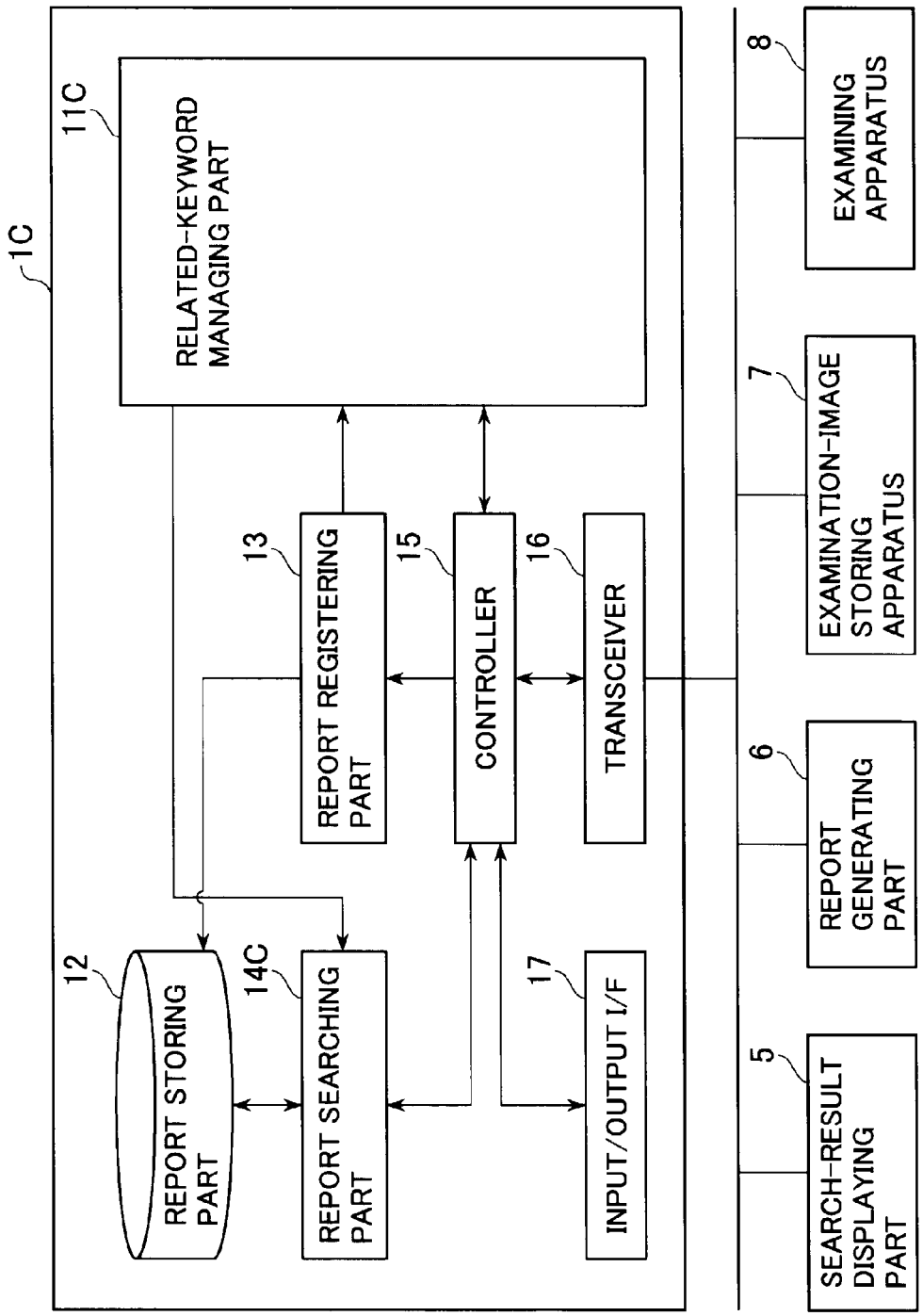

FIG. 15

| SEMANTIC UNIT | | REPORT ID | |
|---|---|---|---|
| LEFT LUNG FIELD — OPACITY | | ID000001 | |
| LEFT LUNG FIELD — GROUND-GLASS | | ID000001 | |
| LUNG ADENOCARCINOMA — LEFT LUNG FIELD | | ID000001 | |
| OPACITY — GROUND-GLASS | | ID000002 | |
| LUNG ADENOCARCINOMA — LEFT LUNG FIELD | | ID000010 | ~R1 |
| LUNG ADENOCARCINOMA — OPACITY | | ID000010 | ~R2 |
| LUNG ADENOCARCINOMA — GROUND-GLASS | | ID000010 | ~R3 |

DIAGNOSTIC REPORT SEARCH SUPPORTING APPARATUS AND DIAGNOSTIC REPORT SEARCHING APPARATUS

CROSS-REFERENCE TO RELATED APPLICATION

This application is based upon and claims the benefit of priority from Japanese Patent Application No. 2009-157983, filed on Jul. 2, 2009; and Japanese Patent Application No. 2010-115906, filed on May 20, 2010; the entire contents of all of which are incorporated herein by reference.

FIELD

Embodiments described herein relate generally to a technique for searching for a diagnostic report generated in the past.

BACKGROUND

Medical practices are divided into special fields, and it is general to request a specialist to interpret a medical image captured with an image diagnosis apparatus. The specialist, namely, a radiologist displays the medical image that the radiologist is requested to interpret, on a monitor such as a liquid crystal display or a CRT (cathode-ray tube) display, and writes a diagnostic report on the result of the interpretation. The radiologist displays a medical image to be compared with the medical image to be interpreted or displays a previous diagnostic report similar in case or diagnosed disease name and uses as a reference material.

A diagnostic report generated in the past is stored in a storing apparatus provided with a hard disk or the like. To read out a diagnostic report to be used as a reference material from the storing apparatus, for example, keyword search by an inputted search term is performed with a searching apparatus (refer to Japanese Unexamined Patent Application Publication No. 2007-293521, for example).

A conventional searching apparatus performs full-text search when searching for a diagnostic report including a similar case or a similar diagnosed disease name. This searching apparatus then presents a list of all diagnostic reports including an inputted term.

This full-text search of referring to text data within diagnostic reports requires a lot of search time and may decrease the efficiency of interpretation. Moreover, even if the full-text search is finished after a lot of time is spent, the value of reference varies depending on the diagnostic reports in the list, and it is hard to determine which diagnostic report is useful. Besides, since the full-text search is search by simple character-string comparison, such a diagnostic report that actually has a relation but is written in a different expression cannot be extracted as the result of the search. Since it is required after the search to display the diagnostic reports in the list one by one and confirm the contents thereof, a lot of time is wasted in finding a desired reference material, and the efficiency of interpretation may be further decreased. In addition, it is difficult to find an appropriate reference material from the list of a huge number of diagnostic reports, so that there is a possibility that any diagnostic report to be referred is not included in the list actually, or there is a case that a diagnostic report that should be truly referred to cannot be confirmed.

BRIEF DESCRIPTION OF THE DRAWINGS

FIG. 1A is a function block diagram of a diagnostic report searching apparatus according to a first embodiment.

FIG. 2 is a schematic view showing an example of a format of a diagnostic report.

FIG. 5 is a data structure view showing an example of a structure of a count table.

FIG. 6C is a schematic view for explaining a flow of information in count of the generated semantic units.

FIG. 8 is an example of a search screen of a diagnostic report searching apparatus.

FIG. 9A is a schematic view for explaining a flow of information in extraction of a semantic unit whose existence number is a predetermined number or more from a count table in diagnostic report searching apparatuses according to the first embodiment and a modified example 3.

FIG. 10A is a function block diagram of a diagnostic report searching apparatus according to a modified example 2.

FIG. 11A is a schematic view for explaining a flow of information in extraction of a semantic unit whose existence number is a predetermined number or more from a count table in the diagnostic report searching apparatus according to the modified example 2.

FIG. 11B is a schematic view for explaining a flow of information in archiving of a semantic unit into a related-keyword library in the diagnostic report searching apparatus according to the modified example 2.

FIG. 12A is a function block diagram of a diagnostic report searching apparatus according to a modified example 3.

FIG. 14A is a function block diagram of a diagnostic report searching apparatus according to a modified example 4

FIG. 15 is a data structure view showing an example of a structure of data archived in a related-report management information archive.

DETAILED DESCRIPTION

Embodiments described herein were devised in consideration of the problems as described above, and an object of the embodiments is to provide a technique for enabling rapid and complete search of previous diagnostic reports to be referred to.

According to the embodiments, a diagnostic report search supporting apparatus and a diagnostic report searching apparatus each have a report registering part, a structuring processing part, a related-term analyzing part, a counting part, and a keyword extracting part. The structuring processing part, for each sentence written in a diagnostic report, extracts terms from the sentence and classifies the terms into predetermined kinds, thereby structuring the sentence written in the diagnostic report. The related-term analyzing part generates combinations each composed of two or more terms based on the plurality of terms extracted by the structuring processing part. The counting part counts the existence number of the same combinations in the plurality of combinations, and extracts combinations whose existence numbers are a predetermined number or more. The keyword extracting part extracts a combination including an inputted desired keyword from among the combinations extracted by the counting part and extracts, as a related keyword, a term other than the desired keyword from the extracted combination.

FIRST EMBODIMENT

Figure 1B:
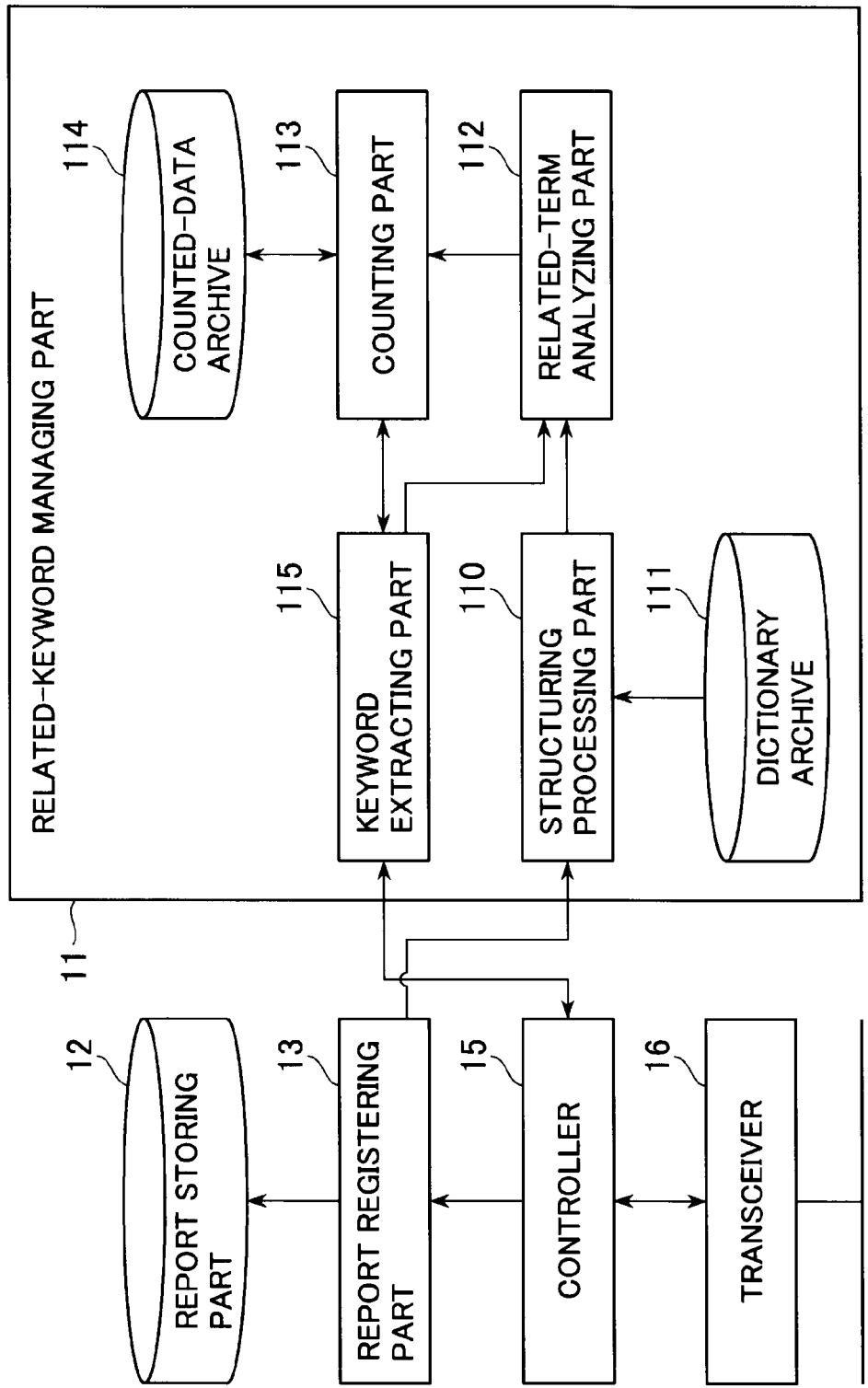
FIG. 1B is a function block diagram showing a detailed configuration of a related-keyword managing part in the diagnostic report searching apparatus according to the first embodiment.
Figure 1C:
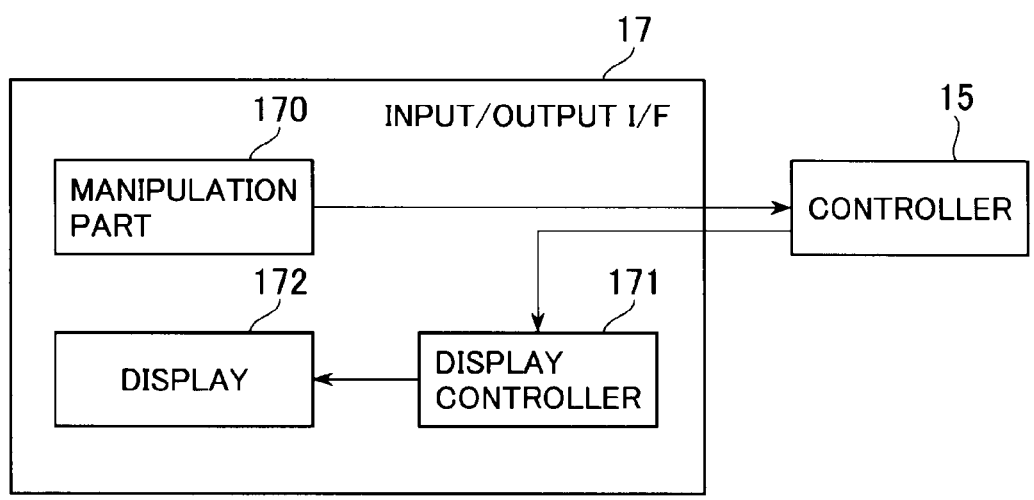
FIG. 1C is a function block diagram showing a detailed configuration of an input/output interface.
Figure 1D:
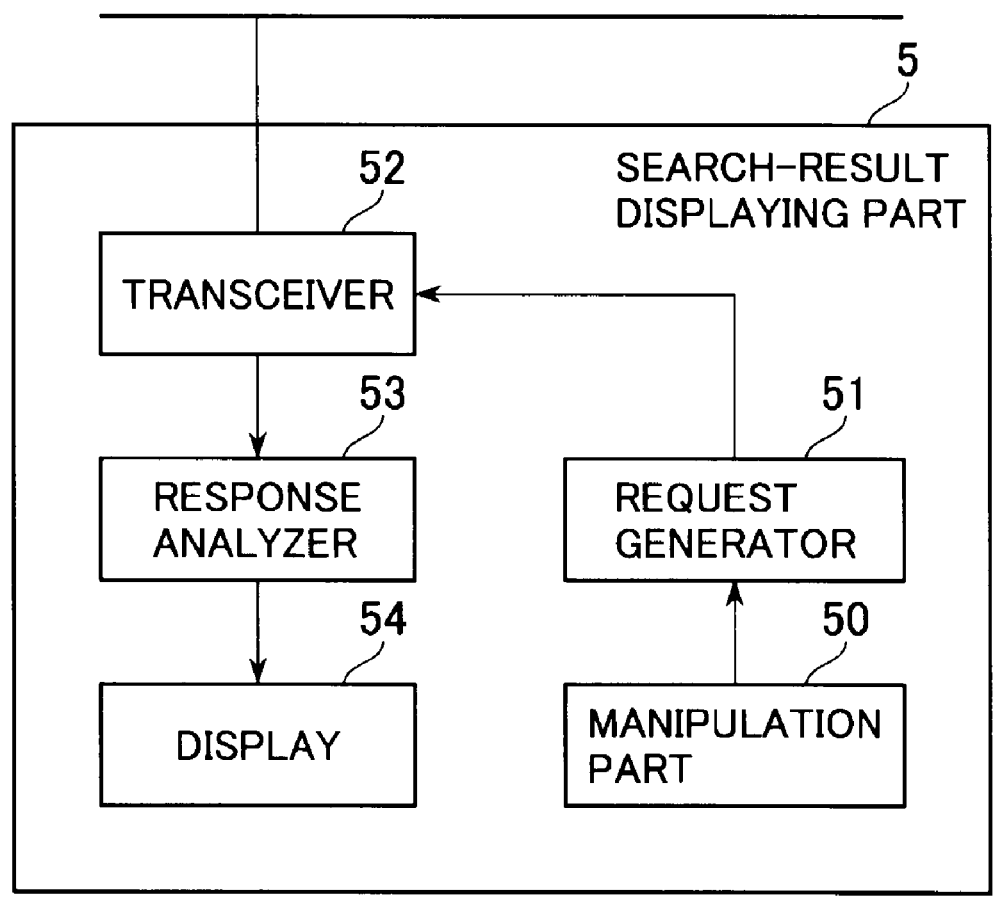
FIG. 1D is a function block diagram showing a detailed configuration of a search-result displaying part.

Below, a configuration and an operation aspect of a diagnostic report searching apparatus according to a first embodiment will be described with reference to FIGS. 1A to 1D. FIG. 1A is a function block diagram of the diagnostic report searching apparatus according to the first embodiment. FIG. 1B is a function block diagram showing a detailed configuration of a related-keyword managing part in the diagnostic report searching apparatus according to the first embodiment. FIG. 1C is a function block diagram showing a detailed configuration of an input/output interface. FIG. 1D is a function block diagram showing a detailed configuration of a search-result displaying part. A "report" will refer to a "diagnostic report" hereinafter.

The diagnostic report searching apparatus according to this embodiment is configured by two operation aspects: "generation of a count table (an operation aspect 1-1)"; and "search by a related keyword (an operation aspect 1-2"). The configuration and the content of operation of the diagnostic report searching apparatus according to this embodiment will be described for the respective operation aspects.

(Operation Aspect 1-1: Generation of Count Table)

The diagnostic report searching apparatus according to this embodiment extracts combinations of closely related terms from findings and diagnoses written in diagnostic reports, generates a table of the combinations, and archives into a counted-data archive as a count table (the count table and the counted-data archive will be described later). As this operation aspect, the configuration and operation relating to generation of the count table will be described.

The diagnostic report searching apparatus according to this embodiment includes at least a report managing part 1 configured to manage and store generated diagnostic reports, and a search-result displaying part 5 configured to request the report managing part 1 to search for a diagnostic report and display the result of the search. The diagnostic report searching apparatus may include a report generating part 6 configured to generate a diagnostic report, an examining apparatus 8 configured to execute an examination and output the result as an image, and an examination-image storing apparatus 7 configured to store the image outputted by the examining apparatus 8. Although the report managing part 1, the search-result displaying part 5, the report generating part 6, the examining apparatus 8, and the examination-image storing apparatus 7 are connected via a network in FIG. 1A, this configuration does not limit the configuration of the diagnostic report searching apparatus, and the respective parts do not need to be independent from each other as separate hardware.

The network is an electronic communication line capable of transmission of electronic data. As the network, for example, a telephone network, an ISDN (Integrated Services Digital Network), an FDDI (Fiber-Distributed Data Interface), an exclusive line, a mobile communication network, a communication satellite line, a CATV (Community Antenna TeleVision), a LAN (Local Area Network), or a combination thereof is employed. In a case that the report managing part 1, the search-result displaying part 5, the report generating part 6, the examining apparatus 8, and the examination-image storing apparatus 7 are connected via the network, the respective parts are capable of data communication with each other by a network communication technique. As the network communication technique, for example, WWW (World Wide Web), TCP/IP protocol (Transmission Control Protocol/Internet Protocol), or DICOM (Digital Imaging and COmmunications in Medicine or the like is employed.

The report generating part 6 includes: an input interface (not shown) including a manipulation part for an operator (a radiologist) to generate a diagnostic report and a display; and a transceiver (not shown) for transmitting a generated diagnostic report to the report managing part 1 described later and requesting the report managing part 1 to store the diagnostic report.

FIG. 2 is a schematic view showing an example of a format of a diagnostic report. This diagnostic report chiefly has a finding field Cs and a diagnosed-disease-name field Ck. In the finding field Cs, a finding that represents determination, comment and so on on the result of interpretation of a medical image is written in the text data format.

In the diagnosed-disease-name field Ck, a diagnosed disease name as a result of interpretation and determination of the medical image is written in the text data format.

Document data of a diagnostic report includes a tag that represents the finding field Cs and a tag that represents the diagnosed-disease-name field Ck. Following the tag representing the finding field Cs, the text data inputted as the finding is written.

Following the tag representing the diagnosed-disease-name field Ck, the text data inputted as the diagnosed disease name is written.

In general, one sentence of the text data inputted into the finding field Cs is composed of a region term wb that represents a target region of the finding, an event term wj that represents an event occurring in the region, a modification term wm that modifies the event term, a certainty term wu that represents the certainty of the event, and particles that connect the terms, in such a manner that "ground-glass opacity is seen in left lung field." There is a case that no modification term wm is included (written).

Further, the text data inputted into the diagnosed-disease-name field Ck is a diagnosed-disease-name term wd such as "lung adenocarcinoma." When the operator inputs such one sentence composed of the region term wb, the event term wj, the modification term wm and the certainty term wu into the finding field Cs by using the manipulation part (now shown), text data representing the one sentence is written into the finding field Cs of a diagnostic report by the report generating part 6. Into the finding field Cs, a plurality of sentences may be inputted.

The diagnostic report generated by the report generating part 6 is archived and managed in the report managing part 1. The report managing part 1 includes a transceiver 16, a report storing part 12, a report registering part 13, a report searching part 14, a controller 15, an input/output interface 17, and a related-keyword managing part 11.

The diagnostic report received from the report generating part 6 is stored into the report storing part 12.

The transceiver 16 is a part configured to execute transmission and reception of data between the report managing part 1 and the outside. The transceiver 16 transmits, to the controller 15, a request and data received from outside, such as a request to store a diagnostic report by the report generating part 6, a request to search for a related keyword having a relation with a keyword designated by the operator (referred to as a "designated keyword" hereinafter), and a request to search for a diagnostic report. The transceiver 16 also transmits, to the source of request, a response to the request by the controller 15, such as the result of the search of a related keyword and the result of the search of a diagnostic report.

Upon reception of a request to store a diagnostic report, the controller 15 transmits the diagnostic report received with the storing request to the report registering part 13 described later, and requests to register the diagnostic report into the report storing part 12.

Further, upon reception of a request to search for a related keyword, the controller 15 transmits, to a keyword extracting part 115 described later, a condition of the search included in the search request, namely, a term for extracting a related keyword and a condition for extracting the related keyword, and receives the related keyword as the result of the search from the keyword extracting part 115. The related keyword having been received is transmitted to the transceiver 16.

Further, upon reception of a request to search for a diagnostic report, the controller 15 transmits, to the report searching part 14 described later, a condition of the search included in the search request, namely, a search keyword (may include the related keyword in addition to the designation keyword), and receives a diagnostic report from the report searching part 14 as the result of the search. The controller 15 transmits the diagnostic report having been received to the transceiver 16.

Further, the controller 15 is also capable of receiving the diagnostic report storing request, the related-keyword search request, or the diagnostic-report search request, from the input/output interface 17 of the report managing part 1. Upon reception of the request from the input/output interface 17, the controller 15 transmits the result to the input/output interface 17 as the source of request.

With reference to FIG. 1C, a configuration of the input/output interface will be described. FIG. 1C is a function block diagram showing a detailed configuration of the input/output interface. The input/output interface 17 includes: a manipulation part 170 for performing registration of a diagnostic report, search of a related keyword or search of a diagnostic report; a display controller 171 configured to process the result of the manipulation with the manipulation part, namely, the result of the search of a related-keyword or the result of the search of a diagnostic report into a predetermined format; and a display 172 configured to display the manipulation result processed by the display controller.

With reference to FIGS. 1A and 1B, upon reception of a request to register a diagnostic report from the controller 15, the report registering part 13 receives the diagnostic report to be registered, from the controller 15, and archives the diagnostic report into the report storing part 12.

Further, the report registering part 13 transmits the received diagnostic report to a structuring processing part 110 described later, and also requests the structuring processing part 110 to perform structuring of a sentence written in the diagnostic report (the sentence will be referred to as a "sentence" hereinafter) (referred to as "structuring of a diagnostic report" hereinafter).

Upon reception of the request for structuring of a diagnostic report, the structuring processing part 110 analyzes the sentence written in the diagnostic report received with the request by comparing the sentence with dictionary data held in a dictionary archive 111, and generates a data structure called a description unit, thereby structuring a diagnostic report (the structured report will be referred to as a "structured report" hereinafter). The structuring of a diagnostic report and the description unit will be described below.

(Structuring of Report)

Figure 3:
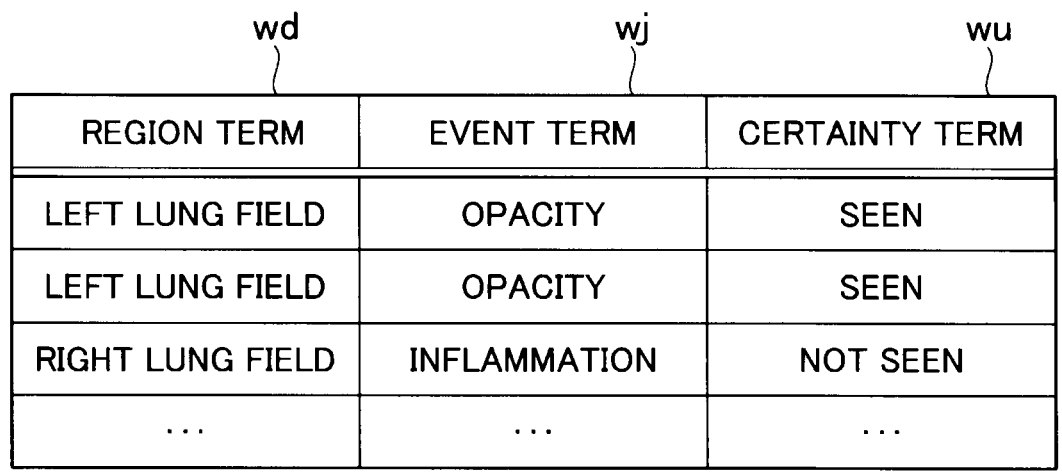
FIG. 3 is a data structure view showing a structure of dictionary data.
Figure 4:
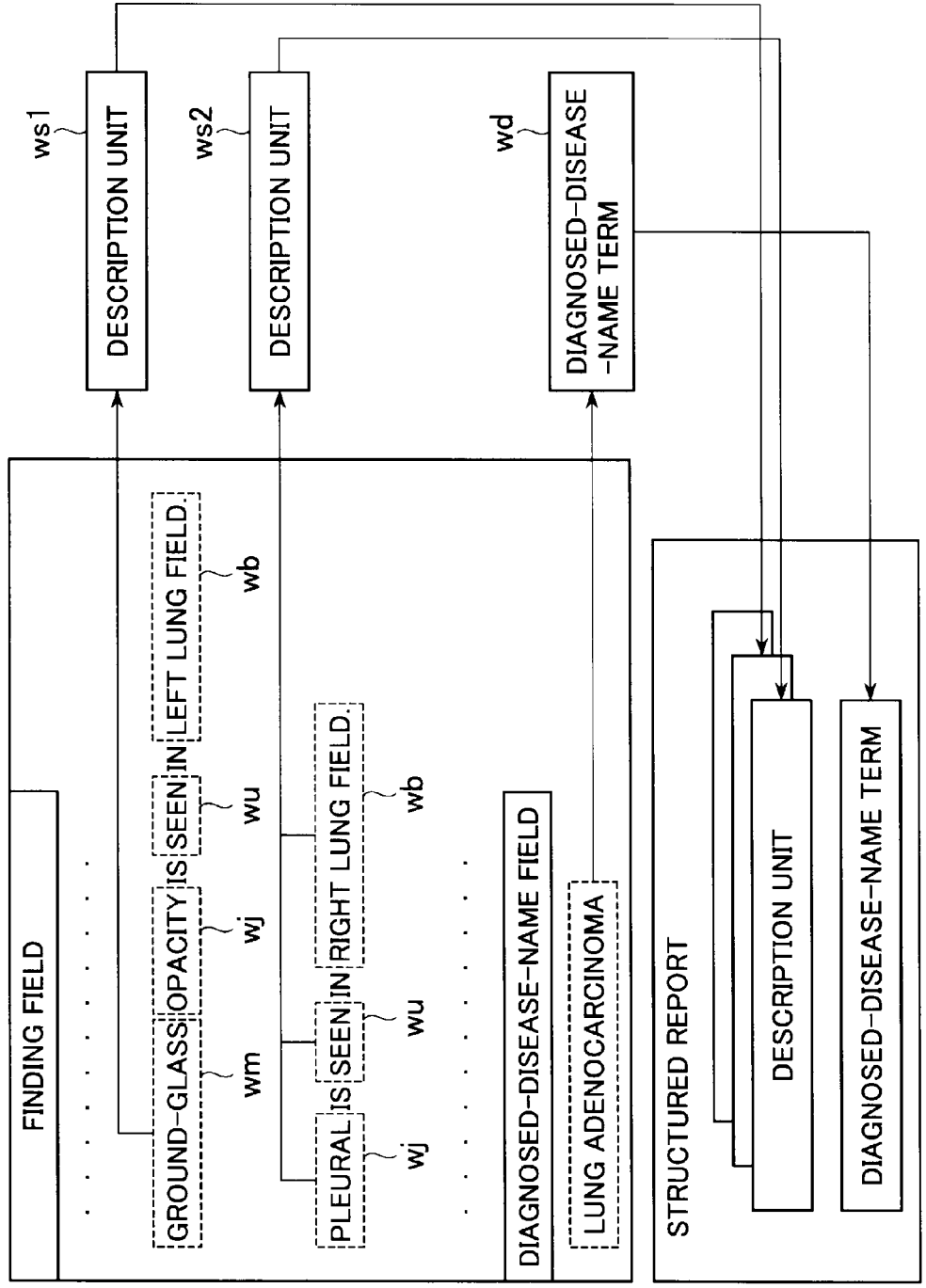
FIG. 4 is a schematic view for explaining a flow of information in generation of a description unit and generation of a structured report.

FIG. 3 is a data structure view showing a data structure of the dictionary data held in the dictionary archive 111. FIG. 4 is a schematic view for explaining a flow of information when structuring a diagnostic report and generating a data structure called a description unit.

When extracting a term, the structuring processing part 110 refers to the dictionary data in order to specify a term to be extracted.

The dictionary data is archived in the dictionary archive 111. As shown in FIG. 3, in the dictionary data, a number of terms each belonging to the region term wb, the event term wj or the certainty term wu are recorded.

As shown in FIG. 4, the structuring processing part 110 reads out an $N^{th}$ sentence (N=1, 2, 3 . . . ) from the finding field Cs of a diagnostic report, performs a syntactic analysis of the sentence having been read out by a syntactic analysis technique such as a morphological analysis to divide the sentence into terms, and compares each of the terms archived in the dictionary data with the sentence while sequentially shifting a comparison position from the beginning to the end of the sentence. In a case that the compared term is included in the sentence, the structuring processing part 110 records the term so as to be included in data of a description unit ws for the sentence being scanned.

By comparing the respective terms recorded in the dictionary data, the structuring processing part 110 extracts the region term wb, the event term wj and the certainty term wu from one sentence.

Moreover, the structuring processing part 110 searches for a modification term that modifies the event term wj based on the result of the syntactic analysis. In a case that there is a modification term that modifies the event term wj, the structuring processing part 110 considers the modification term as a modification term wm.

The extracted region term wb, event term wj and certainty term wu are put into one set. In a case that there is the modification term wm, the modification term wm is included into the one set and recorded into the data of the description unit ws. An explanation of the syntactic analysis technique will be omitted herein. Generation of the data of the description unit ws with the terms extracted from the one sentence put into one set in the above manner provides the terms included in the data of the description unit ws with a semantic connection that forms the one sentence.

In FIG. 4, reference numeral w1 denotes an example of a description unit that includes the modification term wm, whereas reference numeral ws2 denotes an example of a description unit that does not include the modification term wm. Thus, the modification term wm does not need to be always included in the description unit ws.

The structuring processing part 110 repeatedly executes this extraction process on the first-to-last sentences written in the finding field Cs of a diagnostic report and generates data of the description unit ws corresponding to each of the sentences.

Next, the structuring processing part 110 extracts the diagnosed-disease-name term wd from the diagnosed-disease-name field Ck. In a case that there are a plurality of diagnosed-disease-name terms wd in the diagnosed-disease-name field Ck, the structuring processing part 110 extracts all the diagnosed-disease-name terms wd.

With this, structuring of a diagnostic report is completed. Upon completion of structuring of a diagnostic report, the structuring processing part 110 transmits a structured report to a related-term analyzing part 112 and requests generation of a semantic unit.

(Generation of Semantic Unit)

Figure 6A:
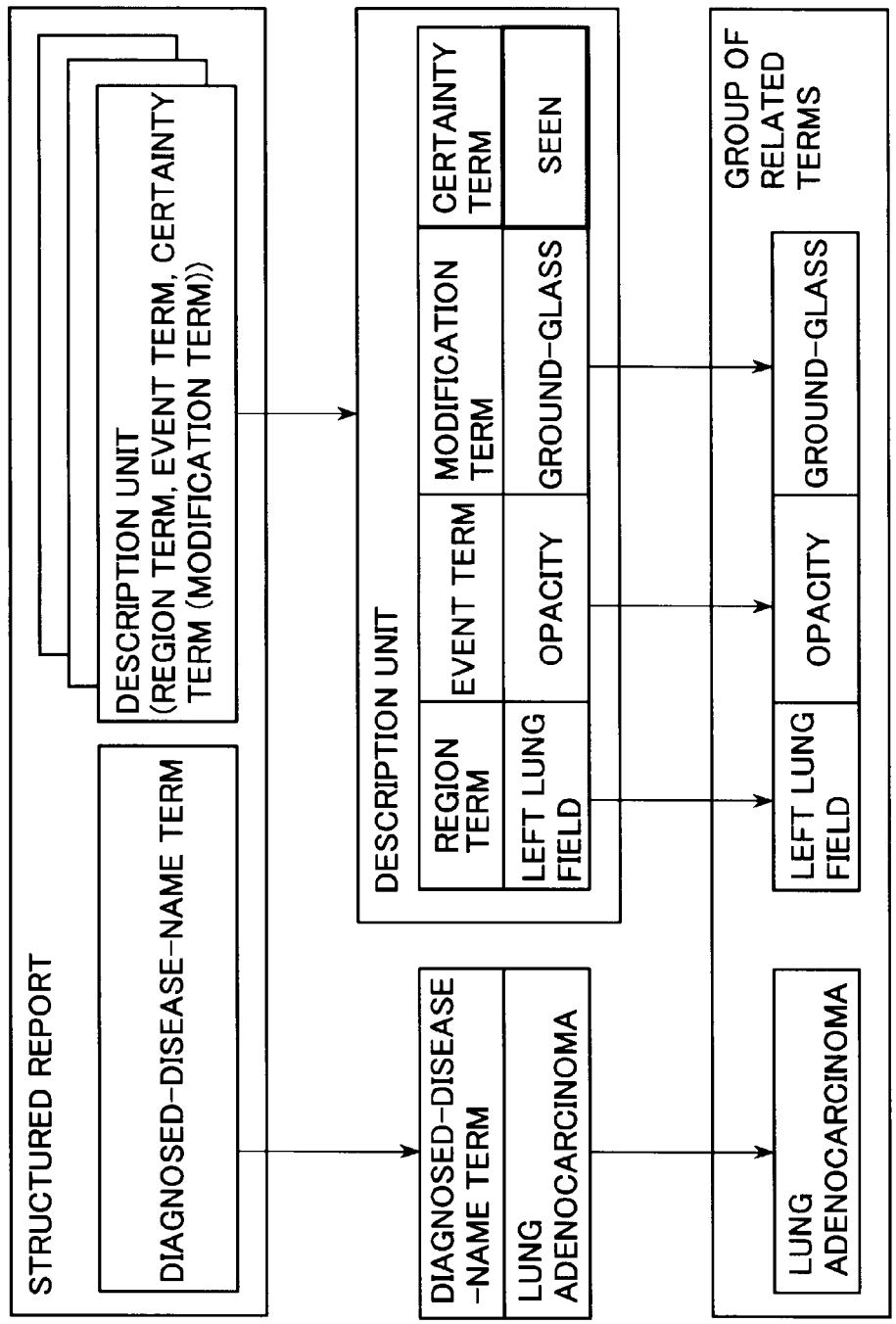
FIG. 6A is a schematic view for explaining a flow of information in extraction of a group of related terms from description units in a structured report.
Figure 6B:
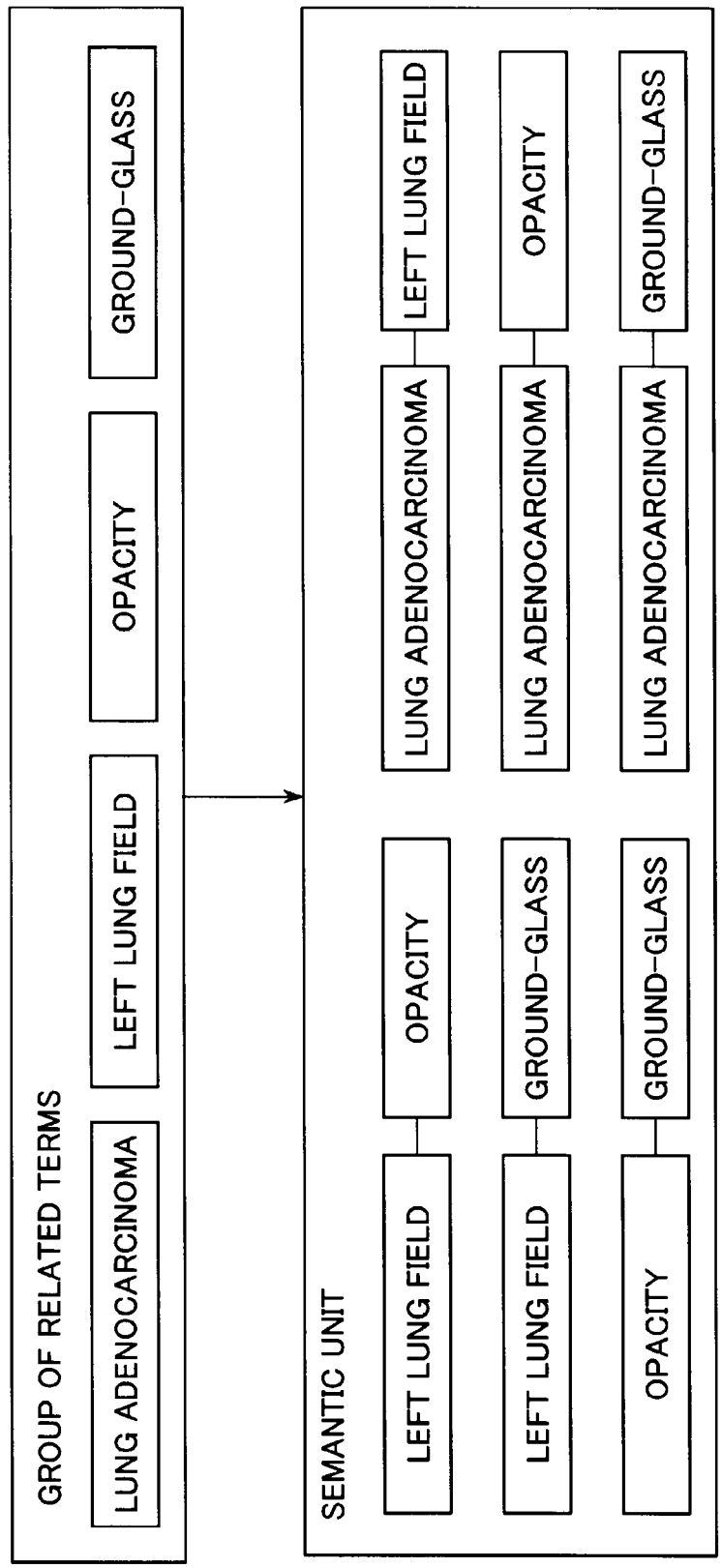
FIG. 6B is a schematic view for explaining a flow of information in generation of a semantic unit from the group of related terms extracted from the description units.

The related-term analyzing part 112 generates a data structure called a semantic unit based on the data of the description unit ws and the term composing the diagnosed-disease-name term wd recorded in the structured report. Below, a semantic unit and a method for generating the semantic unit will be described with reference to FIGS. 5 and 6A to 6C. FIG. 5 is a data structure view showing a structure of a count table. FIGS. 6A to 6C are schematic views for explaining a flow of information when generating semantic units from the description units ws and the diagnosed-disease-name term wd within the structured report and counting the semantic units.

First, FIG. 6A will be referred to. FIG. 6A is a schematic view for explaining a flow of information when extracting a group of related terms from description units within a structured report. Upon reception of a request to generate a semantic unit from the structuring processing part 110, the related-term analyzing part 112 extracts the description units ws and the diagnosed-disease-name term wd recorded in the structured report transmitted with the request.

In extraction of the description units ws, all the description units ws recorded in the structured report may be extracted, or only the description units ws that agree with a determination condition may be extracted by using terms recorded as the region term wb, event term wj, modification term wm or certainty term wu composing the description units ws as the determination condition. For example, in FIG. 6A, such a description unit ws is extracted that a term such as "recognized" or "seen" is recorded as the certainty term wu to represent presence of the event term wj, namely, presence of the finding.

Next, the related-term analyzing part 112 decomposes the extracted description units ws and diagnosed-disease-name term wd into composing terms, respectively, and extracts as a group of related terms. At this moment, all of the terms composing the extracted description units ws and diagnosed disease name term wd may be extracted, or any of the region term wb, event term wj, modification term wm and certainty term wu may be extracted under a certain determination condition. For example, in FIG. 6A, the terms other than the certainty term wu are extracted as the group of related terms.

Next, FIG. 6B will be referred to. FIG. 6B is a schematic view for explaining a flow of information when generating a semantic unit based on a group of related terms extracted from a description unit.

The related-term analyzing part 112 forms combinations each composed of two or more terms from the group of related terms, and generates semantic units so as to avoid overlapping combinations. At this moment, all available combinations may be automatically generated. Alternatively, a condition for generating the combinations, such as "the region term wb and the modification term win will not be combined," may be designated.

A semantic unit is a data structure generated by combining two or more different terms. Generation of this combination from a group of terms having a semantic connection, for example, from a plurality of terms included in one sentence or a plurality of terms designated simultaneously at the time of search enables extraction of, as a related keyword, a term having a relation with a term used as a designation keyword from a semantic unit including the term used as the designation keyword.

In FIG. 6B, all semantic units that can be generated by combining two of four terms of "lung adenocarcinoma (the diagnosed-disease-name term wd)," "left lung field (the region term wb)," "opacity (the event term wj)" and "groundglass (modification term wm)" are generated. In this case, six semantic units are generated consequently ($_6C_2=6!/((6-2)!\cdot2!)=6$).

(Count of Semantic Units and Archiving into Counted-Data Archive)

A counting part 113 counts, of the semantic units generated by the related-term analyzing part 112, how many (referred to as the "existence number" hereinafter) semantic units composed of the same terms exist, combines each of the semantic units with the existence number, and archives into a counted-data archive 114 in the form of a count table. Below, a structure of the count table archived in the counted-data archive 114 and an operation of the counting part 113 will be described with reference to FIGS. 5 and 6C. FIG. 5 is a data structure view showing a structure of the count table. FIG. 6C is a schematic view for explaining a flow of information when counting the generated semantic units.

In the counted-data archive 114, a count table is archived as a logical data structure. In the count table, information of combinations of at least semantic units and the existence numbers of the semantic units is archived. For example, in a case that relational database is used as an information archive, as shown in FIG. 5, lines each composed of a row of semantic unit and a row of existence number are archived in the count table. Hereinafter, "archiving into a count table" refers to putting information of combinations of at least semantic units and the existence numbers of the semantic units into a table and archiving into the counted-data archive 114 in the form of a count table.

The information archived in the count table can be individually retrieved. For example, with reference to FIG. 5 an example, it is possible to retrieve each line including a semantic unit and the existence number thereof, and it is also possible to retrieve a semantic unit or the existence number thereof as individual information.

Moreover, by designating a condition to, for example, retrieve semantic units whose existence numbers are a predetermined number or more (for example, 100 or more), it is possible to retrieve information as a subset that agrees with the condition.

The counting part 113 archives the semantic unit generated by the related-term analyzing part 112 into the count table. At this moment, the counting part 113 firstly searches the count table to confirm whether the semantic unit is already archived therein. In a case that the semantic unit is already archived, the counting part 113 firstly acquires the existence number related with the semantic unit. That is to say, the counting part 113 specifies the existence number of the semantic unit from the row of existence number in the line including the semantic unit. After specifying the existence number of the semantic unit, the counting part 113 adds the number of the semantic unit to be registered to the existence number.

In a case that the semantic unit is not archived, the counting part 113 combines the semantic unit with the existence number, which is the number of the semantic unit to be registered, and newly archives into the count table.

For example, in FIG. 6C, a semantic unit including "left lung field" and "opacity" already exists in the count table, and the counting part 113 adds the number of the semantic unit to be registered, namely, 1 to the existence number 100 of the semantic units to update to 101.

Since a semantic unit including "lung adenocarcinoma" and "left lung field" does not exist in the count table, the counting part 113 puts the number of the semantic units, namely, 1 as the existence number, combines the number with the semantic unit including "lung adenocarcinoma" and "left lung field," and adds the new information to the count table.

Further, the counting part 113 is capable of designating a search condition to retrieve information from the count table. At this moment, it is possible to retrieve each line including a semantic unit and the existence number thereof, and it is also possible to retrieve a semantic unit and the existence number thereof as individual information. In retrieval of the information, it is also possible to set information included in the count table as a search condition, for example, "extracting a semantic unit whose existence number is a predetermined number (for example, 100) or more" and retrieve a subset that agrees with the search condition.

(Operation Aspect 1-2: Search Using Related Keyword)

Next, an operation aspect of extracting a related keyword having a close relation with a designation keyword by using the generated count table and setting a combination of the designation keyword and the related keyword as a search condition, thereby searching for a desired diagnostic report will be described with reference to FIGS. 1D and 8. FIG. 1D is a function block diagram showing a detailed configuration of a search-result displaying part. FIG. 8 is an example of a search screen of the diagnostic report searching apparatus.

The operator performs the search operation of this operation aspect through a manipulation part 50. When the operator displays a search screen by performing an operation of reading out the search screen, a "keyword input field" and a field of "relation selection" are firstly displayed as shown in FIG. 8. Items representing the types of related keywords (referred to as "relation types" hereinafter) are displayed in the field of "relation selection." The operator inputs a designation keyword into the keyword input field, and also selects a relation type to extract regarding the designation keyword, from the items displayed in the field of relation selection.

Related keywords are extracted from an area in the count table corresponding to the relation type selected by the operator. For example, when desiring to extract related keywords extracted from a structured report, the operator checks the item of "finding." The extracted related keywords are displayed in a field of "keyword-extraction-result display" of FIG. 8, by the selected relation types, for example, by types of "inclusion relation" and "similarity relation."

The operator selects a term to be added as a search condition from the related keywords displayed in the field of "keyword-extraction-result display," and presses down a search button, thereby searching for a diagnostic report. Below, the operation aspect will be described in more detail.

Upon reception of an operation by the operator through the manipulation part 50, a request generator 51 generates a search request and transmits the request to a transceiver 52. In the case of extraction of a related keyword, the request generator 51 combines a designation keyword with a relation type selected by the operator through the manipulation part 50 and generates a search request. In the case of search of a diagnostic report, the request generator 51 combines a designation keyword with a related keyword selected by the operator through the manipulation part 50 and generates a search request.

The transceiver 52 transmits the search request received from the request generator 51 to the transceiver 16 of the report managing part 1. Moreover, upon reception of a search result from the transceiver 16 as the result for the search request, the transceiver 52 transmits the search result to a response analyzer 53.

The response analyzer 53 displays the search result received from the transceiver 52 on a display 54 in a predetermined format. In the case of a search result for a related-keyword search request, the response analyzer 53 displays in such a form as written in the field of "keyword-extraction-result display" of FIG. 8.

In the case of a search result for a diagnostic-report search request, the response analyzer 53 displays a list of the searched diagnostic reports. When the operator selects a diagnostic report from the list through the manipulation part, the content of the selected diagnostic report is displayed on the display 54. This operation relating to display of the result of search of a diagnostic report is similar to that of a conventional technique.

Figure 9B:
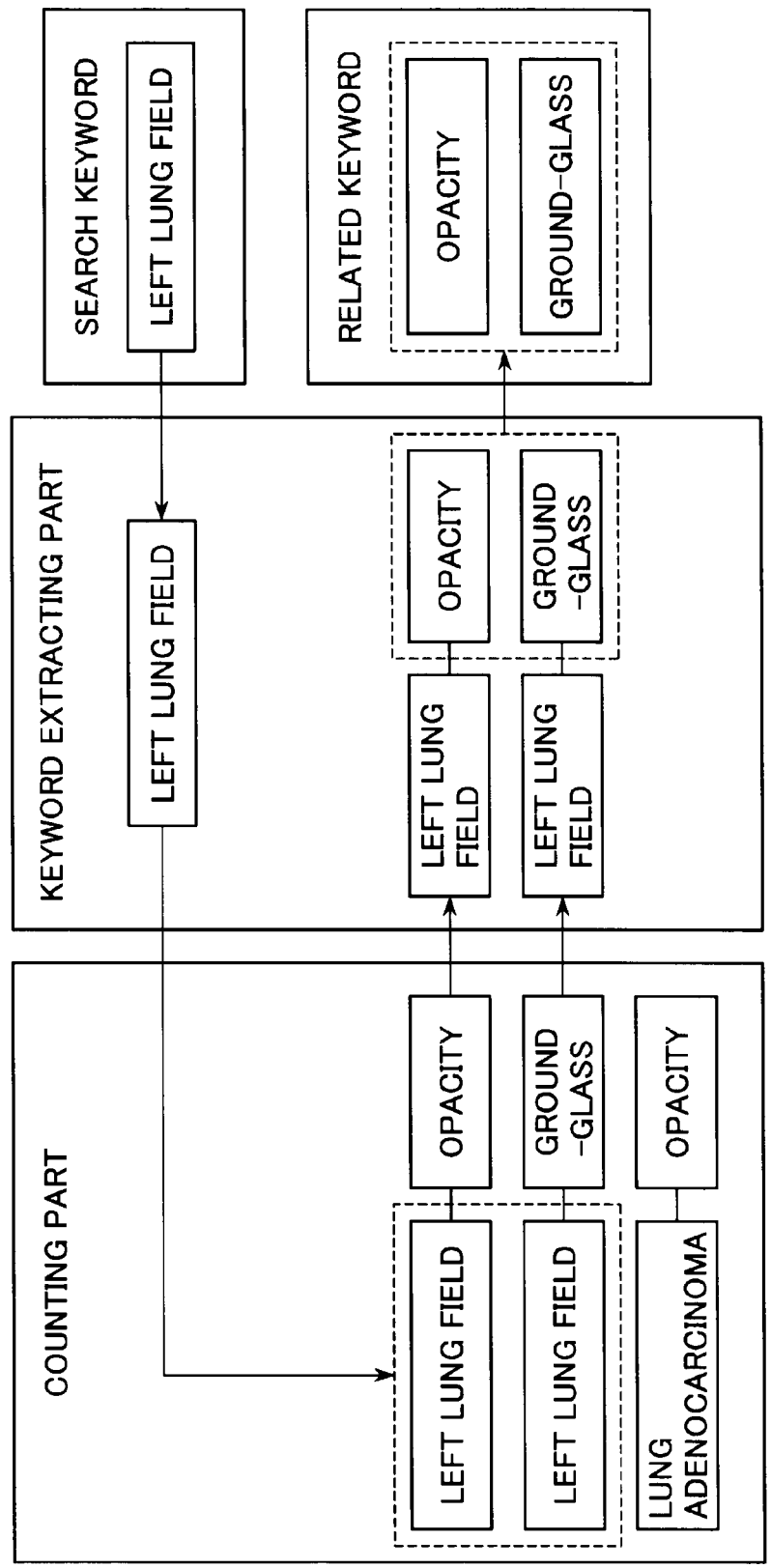
FIG. 9B is a schematic view for explaining a flow of information in extraction of a related keyword having a close relation with a keyword designated by an operator, by using the count table in the diagnostic report searching apparatuses according to the first embodiment and the modified example 3.

An operation aspect in extraction of a related keyword and search of a diagnostic report in the report managing part 1 will be described. Firstly, the operation aspect in extraction of a related keyword will be described with reference to FIGS. 9A and 9B. FIGS. 9A and 9B are schematic views for explaining a flow of information when extracting a semantic unit from the count table and extracting a related keyword from the extracted semantic unit in the diagnostic report searching apparatuses according to this embodiment and a modified example 3. FIG. 9A shows a flow of information when extracting semantic units whose existence numbers are a predetermined number or more from the count table. FIG. 9B shows a flow of information when extracting a related keyword having a close relation with a keyword designated by the operator.

Upon reception of a related-keyword search request from the transceiver 52, the transceiver 16 transmits the search request to the controller 15, and the controller 15 confirms that the search request is a related-keyword search request and transmits the search request to a keyword extracting part 115. In order to determine the type of a request, information including the type of a request can be embedded in a search request. Since such a method is generally known, a description thereof will be omitted herein.

Upon reception of a related-keyword search request, the keyword extracting part 115 retrieves a relation type from the related-keyword search request, transmits the relation type to the counting part 113, and requests extraction of a semantic unit. The counting part 113 extracts a semantic unit in accordance with a previously determined condition (for example, the existence number is 100 or more) from an area in the count table corresponding to the relation type. For example, in a case that "finding" is selected as the relation type, the counting part 113 extracts semantic units compliant with a predetermined condition, for example, semantic units whose existence numbers are 100 or more, from an area in which the semantic unit extracted from the finding field of the diagnostic report is archived.

Next, the keyword extracting part 115 retrieves a designation keyword from the related-keyword search request, and extracts semantic units including the designation keyword from among the semantic units extracted by the counting part 113.

The keyword extracting part 115 decomposes the semantic units including the designation keyword having been extracted into terms composing the respective semantic units, and extracts terms other than a term corresponding to the designation keyword from the obtained group of terms, as related keywords. For example, in FIG. 9B, two semantic units each including the designation keyword "left lung field" are extracted from semantic units whose existence numbers are 100 or more, and related keywords "opacity" and "ground-glass" are obtained as the search result.

The related keywords extracted by the keyword extracting part 115 are transmitted to the controller 15 as the search result, and transmitted, as the result of search of a related-keyword, to the (transceiver 52 of the) search-result displaying part 5 as the source of request via the controller 15 and the transceiver 16.

Next, search of a diagnostic report will be described. Upon reception of a diagnostic report search request from the transceiver 52, the transceiver 16 transmits the search request to the controller 15, and the controller 15 confirms that the search request is a diagnostic report search request and transmits to the report searching part 14.

Upon reception of the diagnostic report search request, the report searching part 14 retrieves a designation keyword and a related keyword from the diagnostic report search request, searches the report storing part 12 with the designation keyword and related keyword as search keywords, and extracts a diagnostic report including the designation keyword and the related keyword.

The diagnostic report extracted by the report searching part 14 is transmitted to the controller 15 as the result of the search and transmitted to the (transceiver 52 of the) search-result displaying part 5 as the source of request via the controller 15 and the transceiver 16, as the result of the search of the diagnostic report.

Thus, by counting semantic units after analyzing the diagnostic report and generating semantic units from terms composing descriptions included in a finding at the time of registering a diagnostic report, it becomes possible to extract semantic units having a close relation. By extracting a related keyword of a designation keyword from the counted semantic units, keywords having a close relation are displayed as related keywords based on the designation keyword.

Consequently, a list of terms having a close relation with a designation keyword is displayed, and it becomes possible to further narrow desired diagnostic reports based on the terms. As a result, a time to check the contents of diagnostic reports to search for a desired diagnostic report is reduced, and moreover, the accuracy of the search is increased.

Further, since related keywords having a close relation with a designation keyword are displayed, it becomes possible to easily consider without missing other possibilities of determination of interpretation.

MODIFIED EXAMPLE 1

Figure 7A:
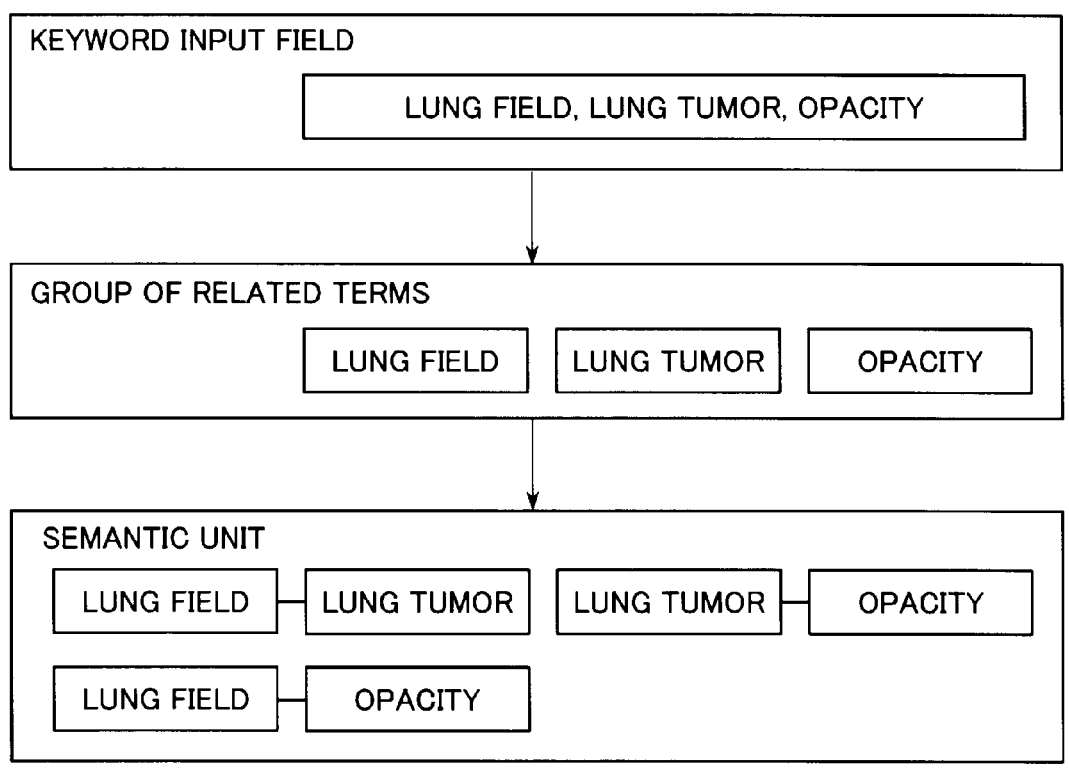
FIG. 7A is a schematic view for explaining a flow of information in generation of a semantic unit from a plurality of terms designated as designation keywords at the time of search.
Figure 7B:
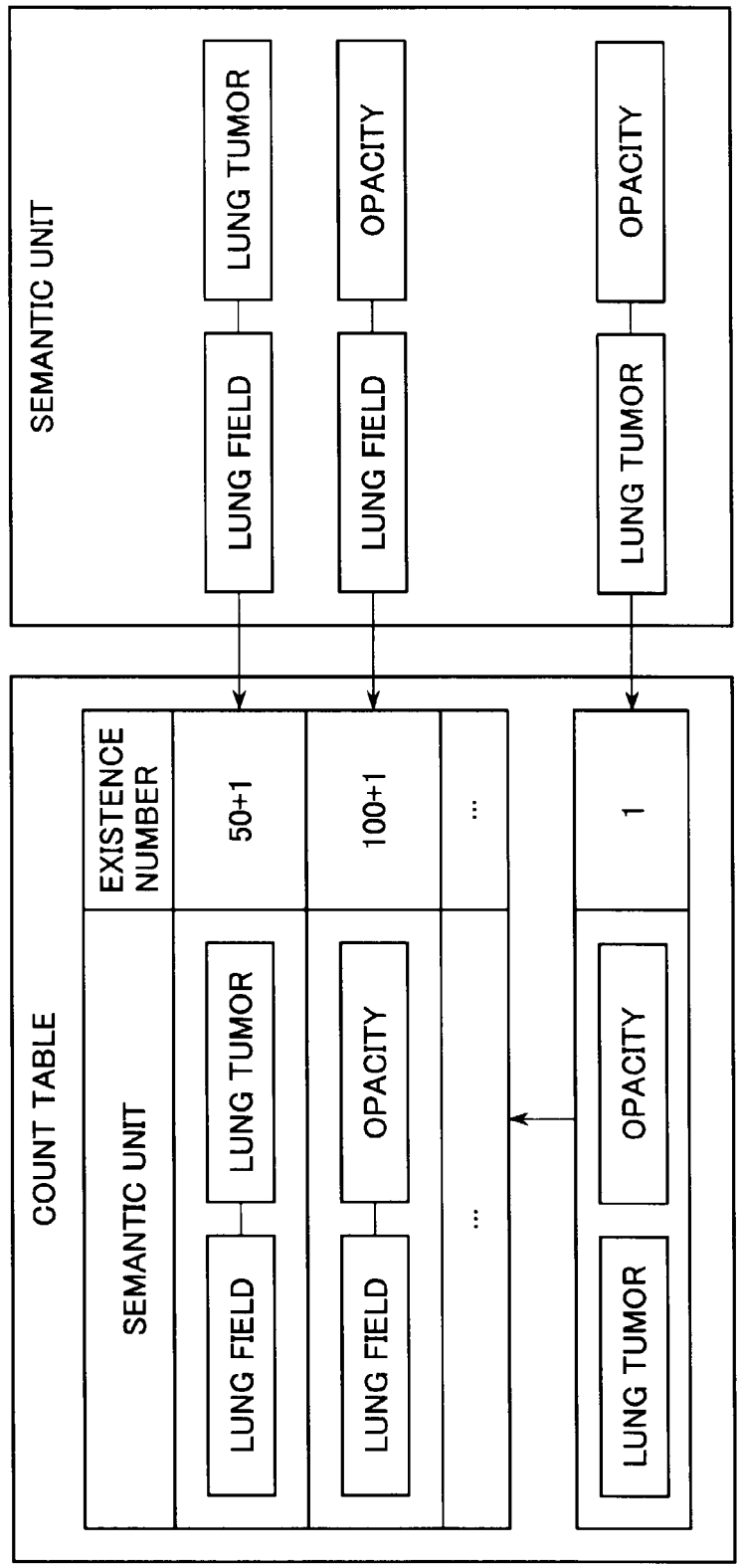
FIG. 7B is a schematic view for explaining a flow of information in count of the semantic units generated from the plurality of terms generated as the designation keywords at the time of search.

Next, a diagnostic report searching apparatus according to a modified example 1 will be described with reference to FIG. 1B and FIGS. 7A and 7B, focusing on a point different from the diagnostic report searching apparatus according to the first embodiment. In the diagnostic report searching apparatus according to the first embodiment, a semantic unit is generated from a structured report.

However, in the diagnostic report searching apparatus according to the modified example 1, not from a structured report but from designation keywords or the like used in search of a diagnostic report, a plurality of terms are acquired, and a semantic unit is generated. The diagnostic report searching apparatus according to the modified example 1 may be configured to be capable of generating a semantic unit from a structured report in a similar manner as the diagnostic report searching apparatus according to the first embodiment. FIGS. 7A and 7B show a flow of information at the time of acquiring, as a group of related terms, a plurality of terms designated as designation keywords to generate a semantic unit. FIG. 7A is a schematic view for explaining a flow of information at the time of generating semantic units from a plurality of terms designated as designation keywords. FIG. 7B is a schematic view for explaining a flow of information at the time of counting the semantic units generated from the plurality of terms designated as the designation keywords.

The related-term analyzing part 112 in the diagnostic report searching apparatus according to the modified example 1 is further capable of receiving a plurality of terms other than a structured report, and generating semantic units with the plurality of terms as a group of related terms. For example, FIG. 7A shows an example of acquiring, as a group of related terms, a plurality of terms designated as designation keywords and generating semantic units. In the example of FIG. 7A, all semantic units that can be generated by combining two of three terms and, in this case, three semantic units are consequently generated ($_3C_2 = 3!/((3-2)!\cdot 2!) = 3$).

As in the method for generating semantic units from designation keywords, the diagnostic report searching apparatus may be configured so that it is possible to previously extract combinations of related terms from a dictionary representing a similarity or inclusion relation between terms or a semantic connection such as a relation between region and case, input the combinations into the related-term analyzing part 112, and register, as semantic units, the connection between the terms representing the similarity or inclusion relation between terms or the semantic connection such as the relation between region and case.

Such a configuration to thus input a plurality of terms other than a group of related terms extracted from a structured report into the related-term analyzing part 112 is equivalent to a keyword inputting part. For example, in the case of inputting designation keywords used in search of a diagnostic report into the related-term analyzing part 112, the apparatus can be configured to include the keyword extracting part 115 as the keyword inputting part. Moreover, for example, in the case of inputting a combination of related terms extracted from the aforementioned dictionary, the apparatus can be configured to further include another part as the keyword inputting part.

The generated semantic units are counted by the counting part 113 and the existence number thereof is archived into the count table, as in the diagnostic report searching apparatus according to the first embodiment. In this case, all the generated semantic units including those generated from a structured report may be registered into the same area of the count table described later. Alternatively, the semantic units may be archived into archive areas divided by the types such as the similarity relation and the inclusion relation.

By making it possible to archive semantic units into the count table in archive areas divided by the information retrieval sources, usages or types such as the similarity relation and the inclusion relation, it becomes possible to designate the archive area (the type) in extraction of semantic units and thereby extract semantic units separately by the archive areas (the types, sources of retrieval, or usages). In the case of generating semantic units from designation keywords and archiving as shown in FIG. 7B, by generating an archive area different from that of semantic units generated from a structured report, for example, generating a search-history count table in the counted-data archive 114 and archiving semantic units generated from designation keywords therein, it is possible to manage the semantic units generated from the designation keywords separately from the semantic units generated from the structured report.

In the case of generating semantic units from designation keywords, it is possible to configure to generate semantic units at all searches, or it is possible to dispose a check box on an input field so that the operator can select whether or not to generate semantic units.

Further, it is possible to configure to separately archive a search history, that is, archive designation keywords designated simultaneously at the time of search as a history at timing of every search, and generate semantic units from the search history at different timing from the timing of search. To be specific, a process of extracting semantic units from a search history is added as a function, and the apparatus may be configured so that, in response to a request to execute the function from the operator through the manipulation part, the related-term analyzing part 112 generates semantic units from the search history, and the counting part 113 archives the generated semantic units into the count table.

Further, in the above example, a plurality of terms to become the base of generation of semantic units can be a plurality of terms having a semantic connection, and are not limited to a plurality of terms inputted into a search history. For example, the apparatus may be configured to be capable of generating semantic units from a plurality of terms having a semantic connection that have been inputted by the operator.

Accordingly, it is possible to generate semantic units from a combination of terms having a semantic connection, other than a structured report, for example, from a plurality of designation keywords having been simultaneously designated at the time of search of a diagnostic report or from a plurality of terms having a similarity relation or inclusion relation, and register the semantic units into the count table, thereby searching for a diagnostic report by using the registered semantic units.

MODIFIED EXAMPLE 2

Figure 10B:
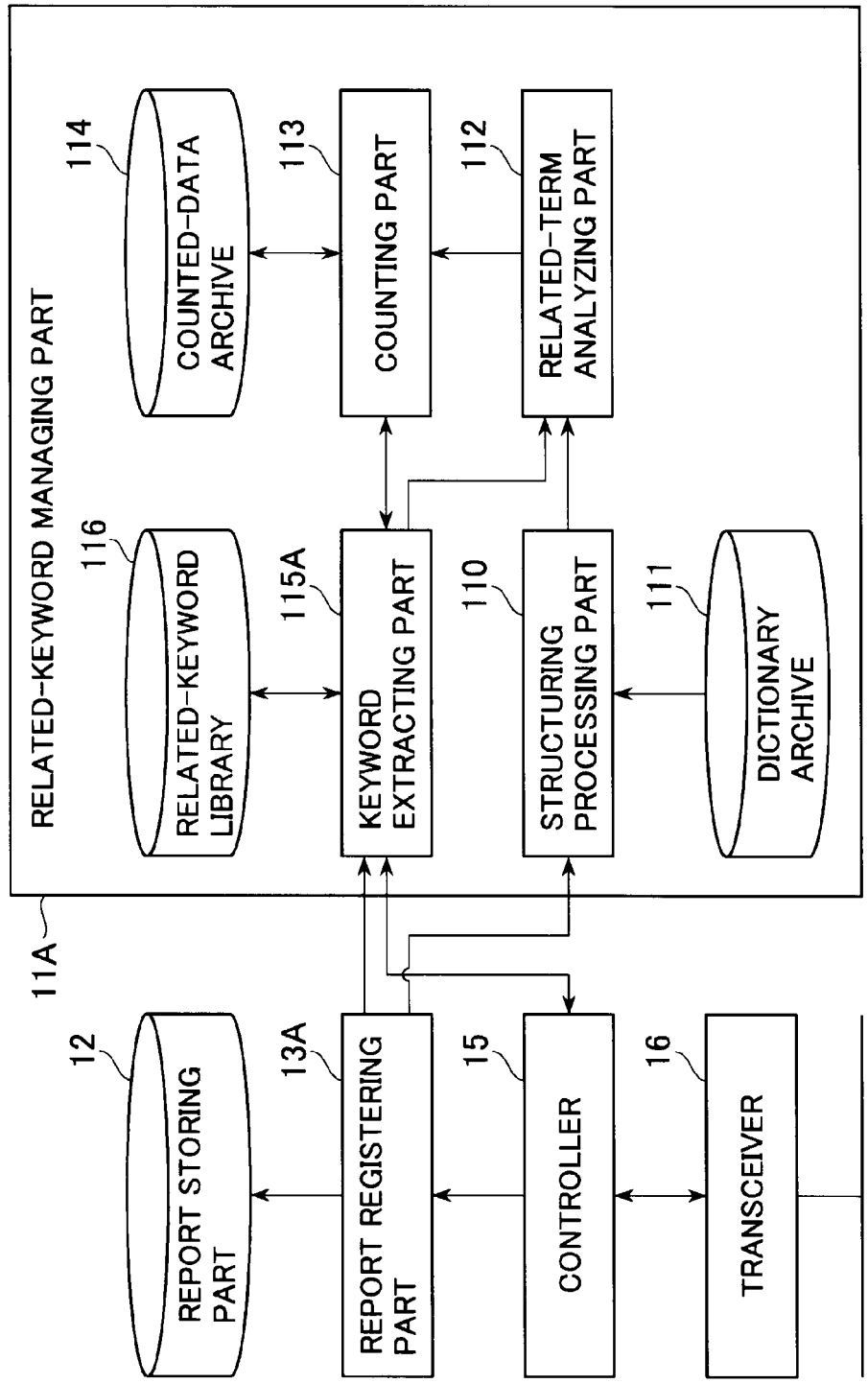
FIG. 10B is a function block diagram showing a detailed configuration of a related-keyword managing part in the diagnostic report searching apparatus according to the modified example 2.

Next, a configuration and operation aspect of a diagnostic report searching apparatus according to a modified example 2 will be described with reference to FIGS. 10A and 10B. FIG. 10A is a function block diagram of the diagnostic report searching apparatus according to the modified example 2. FIG. 10B is a function block diagram showing a detailed configuration of a related-keyword managing part in the diagnostic report searching apparatus according to the modified example 2.

In the diagnostic report searching apparatus according to the modified example 2, an operation aspect up to generation of a report is similar to the operation aspect (the operation aspect 1-1) in the diagnostic report searching apparatus according to the first embodiment. The diagnostic report searching apparatus according to the modified example 2 is different in that, in registration of a diagnostic report, not only the count table is generated but also a related-keyword library 116 is generated by a keyword extracting part 115A and a related keyword is extracted from the related-keyword library 116. Below, the diagnostic report searching apparatus will be described, focusing on a point different from the diagnostic report searching apparatus according to the first embodiment.

When the operator registers a diagnostic report through the report generating part 6, a request to register the diagnostic report is transmitted to a report registering part 13A via the transceiver 16 and the controller 15. Since an operation performed at this moment is similar to that of the diagnostic report searching apparatus according to the first embodiment, a description thereof will be omitted.

Upon reception of the request to register the diagnostic report from the controller 15, the report registering part 13A receives the diagnostic report to be registered from the controller 15 to archive into the report storing part 12, and also transmits the received diagnostic report to the structuring processing part 110 to request structuring of the diagnostic report. This operation is similar to that of the report registering part 13.

When the structuring processing part 110 is requested to structure the diagnostic report, a count table is generated via the related-term analyzing part 112 and the counting part 113. Since this operation is also similar to that of the diagnostic report searching apparatus according to the first embodiment, a description thereof will be omitted herein.

Figure 11C:
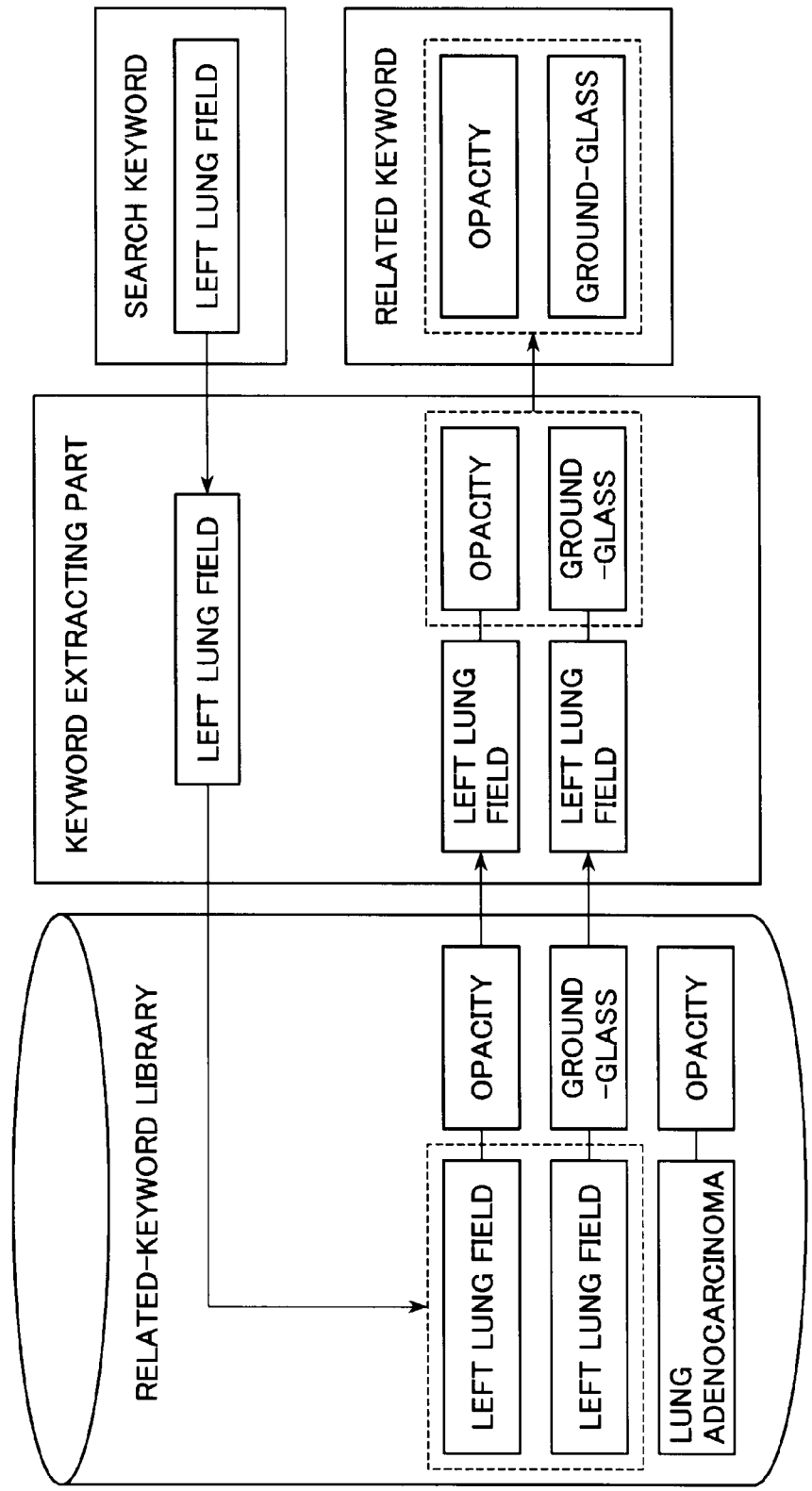
FIG. 11C is a schematic view for explaining a flow of information in extraction of a related keyword having a close relation with a keyword designated by an operator by using the related-keyword library in the diagnostic report searching apparatus according to the modified example 2.

When receiving the request to register the diagnostic report from the controller 15, the report registering part 13A further requests a keyword extracting part 115A described later to generate a related-keyword library. Generation of the related-keyword library will be described with reference to FIGS. 11A to 11C as well as FIGS. 10A and 10B. FIG. 11A is a schematic view for explaining a flow of information at the time of extracting a semantic unit whose existence number is a predetermined number or more from the count table in the diagnostic report searching apparatus according to the modified example 2. FIG. 11B is a schematic view for explaining a flow of information at the time of archiving the semantic unit into the related-keyword library in the diagnostic report searching apparatus according to the modified example 2. FIG. 11C is a schematic view for explaining a flow of information at the time of extracting a related keyword having a close relation with a keyword designated by an operator using the related-keyword library in the diagnostic report searching apparatus according to the modified example 2.

The related-keyword library 116 is an area in which a semantic unit extracted from the count table under a predetermined condition, for example, a condition that the archive number is 100 or more, is archived. The entity of data representing the semantic unit extracted from the count table may be archived, or a reference (for example, a link) to the semantic unit compliant with the predetermined condition on the count table may be archived.

Further, in a case that the count table is divided into areas in which semantic units are archived by the relation types, the related-keyword library 116 may be configured in a manner that semantic units can be archived into areas divided by the relation types, as in the count table.

Upon reception of the related-keyword generation request, the keyword extracting part 115A causes the counting part 113 to extract semantic units from the count table under a previously determined condition, and acquires the semantic units from the counting part 113.

With reference to FIGS. 11A and 11B as an example, as shown in FIG. 11A, the keyword extracting part 115A firstly causes the counting part 113 to extract semantic units whose existence numbers are 100 or more from the count table.

Next, the keyword extracting part 115A archives the semantic units acquired from the counting part 113 into the related-keyword library 116 as shown in FIG. 11B. In a case that the count table has divided areas to archive semantic units by the relation types, the keyword extracting part 115A archives the acquired semantic units into areas in the related-keyword library divided by the areas of the acquisition sources (divided by the relation types) in the count table.

For example, in a case that a semantic unit is archived in an area of "finding" in the count table, an area of "finding" is generated in the related-keyword library and the semantic unit is archived therein.

At the time of search of a related keyword, the keyword extracting part 115A receives a request to search for a related keyword from the controller 15, similarly to the keyword extracting part 115.

Upon reception of the related-keyword search request, the keyword extracting part 115A retrieves a designation keyword and a relation type from the related-keyword search request, and extracts a semantic unit including the designation keyword from an area in the related-keyword library corresponding to the relation type.

Upon extraction of the semantic unit, the keyword extracting part 115A decomposes the semantic unit into composing terms, and transmits to the controller 15 as the source of request with a term other than the designation keyword as a related keyword.

With reference to FIG. 11 as an example, the keyword extracting part 115A extracts two semantic units including "left lung field" of the designation keyword from the related-keyword library and extracts, as related keywords, terms other than "left lung field" of the designation keyword, namely, "opacity" and "ground-glass" from terms composing the semantic units.

Accordingly, since the diagnostic report searching apparatus according to the modified example 2 is configured to, in registration of a diagnostic report, count semantic units, for example, extract semantic units whose registration numbers are 100 or more in advance, it is possible to reduce a processing load in search of a related keyword, as compared with the diagnostic report searching apparatus according to the first embodiment.

Since the configuration and operation relating to search of a diagnostic report is similar to that of the diagnostic report searching apparatus according to the first embodiment, a description will be omitted.

MODIFIED EXAMPLE 3

Figure 12B:
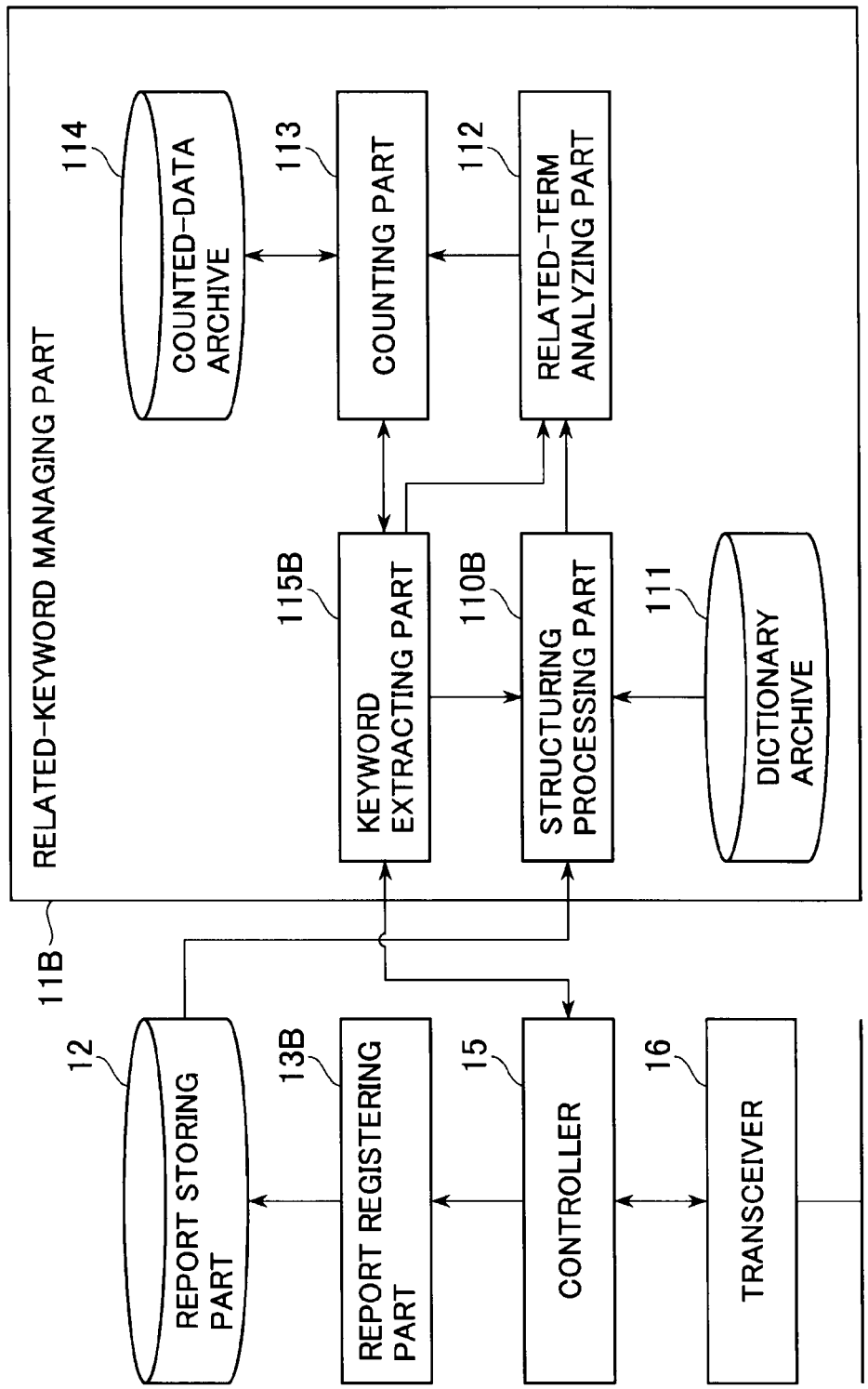
FIG. 12B is a function block diagram showing a detailed configuration of a related-keyword managing part in the diagnostic report searching apparatus according to the modified example 3.

Next, a configuration and operation aspect of a diagnostic report searching apparatus according to a modified example 3 will be described with reference to FIGS. 12A and 12B. FIG. 12A is a function block diagram of the diagnostic report searching apparatus according to the modified example 3. FIG. 12B is a function block diagram showing a detailed configuration of a related-keyword managing part in the diagnostic report searching apparatus according to the modified example 3.

The diagnostic report searching apparatus according to the modified example 3 is different in that structuring of a diagnostic report, generation of a semantic unit, and generation of a count table are executed not at the time of registration of a diagnostic report but at the time of search of a related keyword. Below, the diagnostic report searching apparatus will be described, focusing on a different point from the diagnostic report searching apparatus according to the first embodiment.

When the operator (the radiologist) registers a diagnostic report through the report generating part 6, a request to register the diagnostic report is transmitted to a report registering part 13B via the transceiver 16 and the controller 15. Since an operation performed at this moment is similar to that of the diagnostic report searching apparatus according to the first embodiment, a description thereof will be omitted.

Upon reception of the request to register the diagnostic report from the controller 15, the report registering part 13B receives the diagnostic report to be registered from the controller 15 and archives into the report storing part 12. Unlike the report registering part 13, the report registering part 13B does not request to structure the diagnostic report. That is to say, structuring of a diagnostic report, generation of a semantic unit, and generation of a count table are performed not at the time of registration of the diagnostic report but following search of a related keyword.

Similarly to the keyword extracting part 115, a keyword extracting part 115B receives a request to search for a related keyword from the controller 15 at the time of search of a related-keyword.

Upon reception of the related-keyword search request, the keyword extracting part 115B requests a structuring processing part 110B described later to structure a diagnostic report. In response to the diagnostic-report structuring request, the diagnostic report archived in the report storing part 12 is structured by the structuring processing part 110B, and archived into a generated count table via the related-keyword analyzing part 112 and the counting part 113.

Since the operation by the related-term analyzing part 112 and the counting part 113 of generating a semantic unit from a structured report and archiving the semantic unit into the count table is similar to that of the diagnostic report searching apparatus according to the first embodiment, a description thereof will be omitted.

When the count table is generated following the diagnostic report structuring request, the keyword extracting part 115B retrieves a relation type from the related-keyword search request, transmits the relation type to the counting part 113, and also requests the counting part 113 to extract semantic units. When extraction of semantic units by the counting part 113 is completed, the keyword extracting part 115B retrieves a designation keyword from the related-keyword search request, and extracts a related keyword from among the semantic units extracted by the counting part 113. Since this operation is similar to that of the keyword extracting part 115, a detailed description thereof will be omitted.

Structuring of a report in the diagnostic report searching apparatus according to the modified example 3 will be described in more detail. The structuring processing part 110B is similar to that of the first embodiment in structuring of a diagnostic report by comparing the diagnostic report with the dictionary data held in the dictionary archive 111, analyzing, and generating a data structure called a description unit. However, the structuring processing part 110B is different from that of the first embodiment in a diagnostic report to structure.

In response to the diagnostic report structuring request from the keyword extracting part 115B, the structuring processing part 110B extracts the diagnostic report from the report storing part 12 and structures the extracted diagnostic report. In this case, all the diagnostic reports archived in the report storing part 12 may be structured, or part thereof may be extracted under a designated condition, such as acquiring a designation keyword included in a related-keyword search request from the keyword extracting part 115B and extracting diagnostic reports including the designation keyword.

Figure 13A:
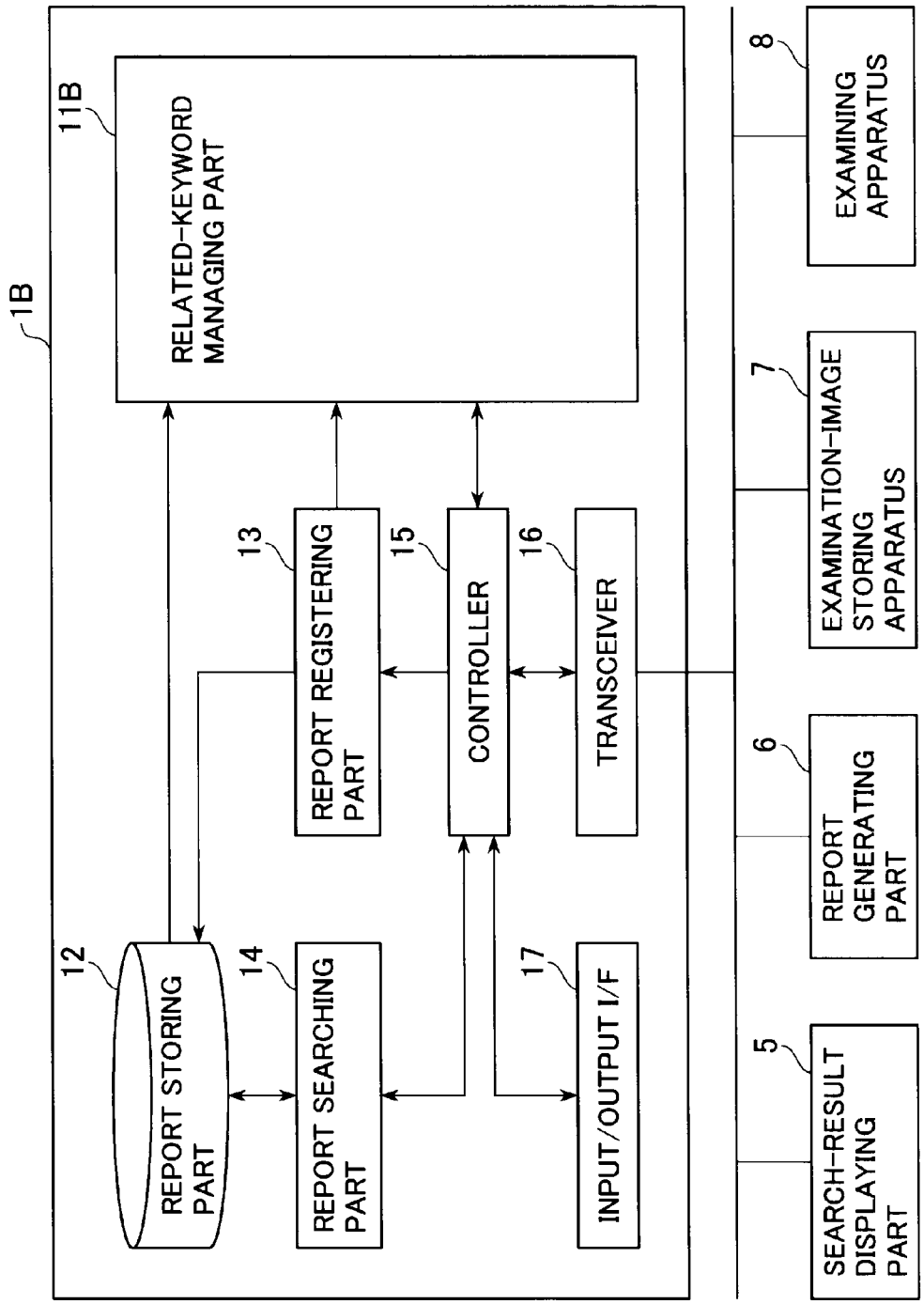
FIG. 13A is a function block diagram of a diagnostic report searching apparatus according to a modified example 3A.
Figure 13B:
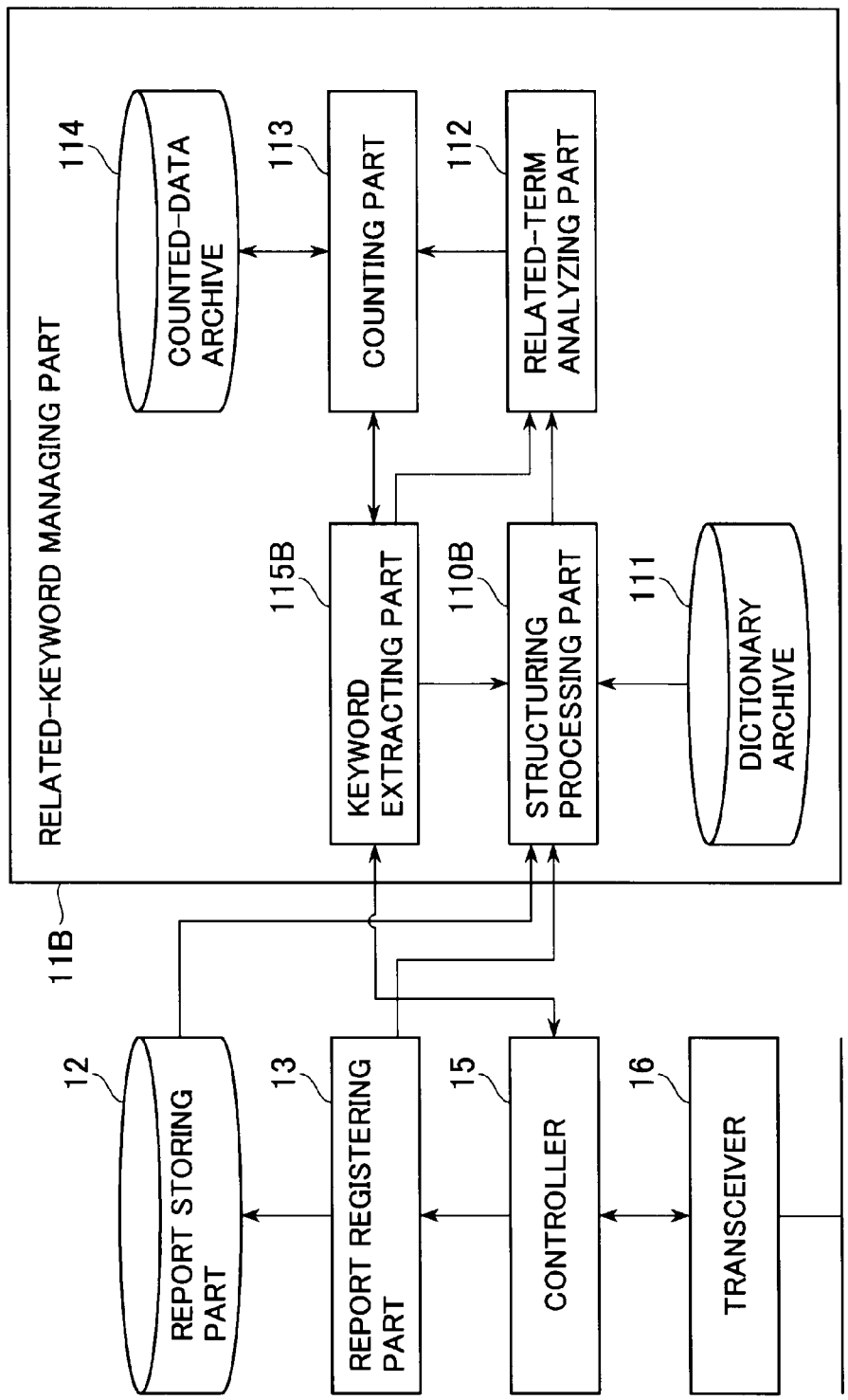
FIG. 13B is a function block diagram showing a detailed configuration of a related-keyword managing part in the diagnostic report searching apparatus according to the modified example 3A.

In the above example, every time a related keyword is searched for, structuring of a diagnostic report, generation of a semantic unit, and generation of a count table are performed. However, the report registering part 13B may be replaced with the report registering part 13 of the diagnostic report searching apparatus according to the first embodiment as shown in block diagrams of FIGS. 13A and 13B, for example (this configuration will be a modified example 3A). FIG. 13A is a function block diagram of a diagnostic report searching apparatus according to the modified example 3A. FIG. 13B is a function block diagram showing a detailed configuration of a related-keyword managing part in the diagnostic report searching apparatus according to the modified example 3A. In this case, the diagnostic report searching apparatus may be configured to structure diagnostic reports from the report storing part 12 only at the start and, after a count table is generated, structure diagnostic reports to be registered at the time of diagnostic report registration.

Further, in the above example, when a related keyword is searched for, structuring of a diagnostic report, generation of a semantic unit, and generation of a count table are performed. However, in the case of structuring diagnostic reports from the report storing part 12 only at the start as shown in FIGS. 13A and 13B, there is no need to always perform when a related keyword is searched for, and the apparatus may be configured to be capable of generating a count table before executing search by operation with the manipulation part.

Accordingly, by making it possible to structure a diagnostic report archived in the report storing part 12 as in the diagnostic report searching apparatus according to the modified example 3, for example, it becomes possible to structure a diagnostic report generated by another apparatus in the past and archived in the report storing part 12 to extract semantic units and generate a count table, thereby searching by a related keyword.

MODIFIED EXAMPLE 4

Figure 14B:
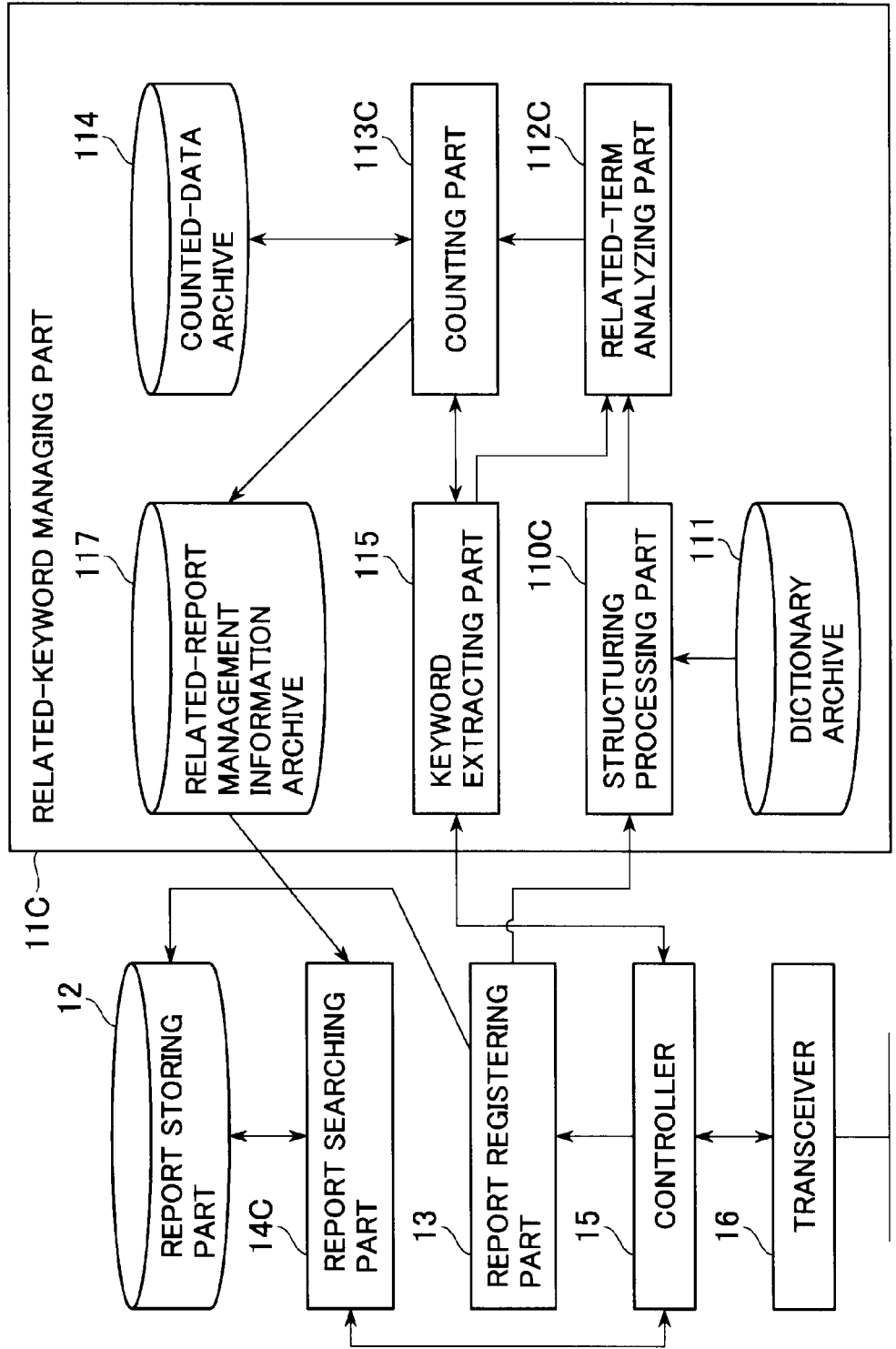
FIG. 14B is a function block diagram showing a detailed configuration of a related-keyword managing part in the diagnostic report searching apparatus according to the modified example 4.

Next, a configuration and operation aspect of a diagnostic report searching apparatus according to a modified example 4 will be described with reference to FIGS. 14A and 14B. FIG. 14A is a function block diagram of the diagnostic report searching apparatus according to the modified example 4. FIG. 14B is a function block diagram showing a detailed configuration of a related-keyword managing part in the diagnostic report searching apparatus according to the modified example 4.

The diagnostic report searching apparatus according to the modified example 4 is different in generating a related-report management information archive 117 when generating a count table. In the related-report management information archive 117, semantic units registered in the count table are registered, related with identification information (referred to as a "report ID" hereinafter) such as a report ID for identifying a diagnostic report as the source of extraction of the semantic units. In the diagnostic report searching apparatus according to the modified example 4, a report searching part 14C is capable of extracting a diagnostic report from the report storing part 12 based on a report ID related with a semantic unit including a search keyword and a related keyword. Below, the diagnostic report searching apparatus will be described, focusing on a point different from the diagnostic report searching apparatus according to the first embodiment.

In response to a request to structure a diagnostic report, a structuring processing part 110C generates a data structure called a description unit from the diagnostic report received together with the request, thereby structuring the diagnostic report received together with the request. This operation is similar to that of the first embodiment.

When structuring of the diagnostic report is completed, the structuring processing part 110C transmits a structured report to a related-term analyzing part 112C and requests to generate semantic units. At this moment, the structuring processing part 110C adds a report ID of the diagnostic report to the structured report and transmits to the related-term analyzing part 112C.

The related-term analyzing part 112C generates a data structure called a semantic unit from the data of the description unit ws and the term composing the diagnosed-disease-name term wd recorded in the structured report. This operation is similar to that of the first embodiment.

The related-term analyzing part 112C transmits the generated semantic units to a counting part 113C.

The semantic units generated by the related-term analyzing part 112C are archived into the count table after the existence numbers of the respective semantic units are counted by the counting part 113C, and the semantic units and the existence numbers are combined, respectively. This operation is similar to that of the first embodiment.

The counting part 113C of the modified example 4 generates the related-report management information archive 117 when generating the count table.

In the related-report management information archive 117, information is archived in a manner that at least semantic units and report IDs of diagnostic reports as the source of extraction of the semantic units are combined. FIG. 15 is a data structure view showing an example of a structure of data archived in the related-report management information archive. For example, in a case that relational database is used as a part in which information is archived, lines each having a row of semantic unit and a row of report ID are archived as shown in FIG. 15.

The counting part 113C archives the semantic unit generated by the related-keyword analyzing part 112C into the count table. At this moment, the counting part 113C firstly searches the count table to confirm whether the semantic unit is already archived. In a case that the semantic unit is already archived, the counting part 113C firstly acquires the existence number related with the semantic unit. That is to say, the counting part 113C specifies the existence number of the semantic unit from the row of existence number of a line including the semantic unit. After specifying the existence number of the semantic unit, the counting part 113C adds the number of the semantic unit to be registered to the existence number. In a case that the semantic unit is not archived, the semantic unit and the existence number are combined with the number of the semantic unit to be registered as the existence number, and newly archived into the count table.

Further, the counting part 113C relates each semantic unit generated by the related-term analyzing part 112C with the report ID received together with the semantic unit from the related-term analyzing part 112C, and archives into the related-report management information archive 117 as related-report management information. In the example of FIG. 15, related-report management information R1 to R3, in which the respective semantic units generated by the related-term analyzing part 112C are related with a report ID "ID000010," are archived into the related-report management information archive 117.

In the case of previously searching the related-report management information archive 117 when registering related-report management information into the related-report management information archive 117 and confirming that related-report management information having the same combination of semantic unit and report ID is already archived, the counting part 113C may be configured not to archive the related-report management information having the same combination. Moreover, the counting part 113C may be configured, regardless of whether the related-report management information having the same combination is archived or not, to archive related-report management information into the related-report management information archive 117 (in this case, the counting part 113C may be configured not to search the related-report management archive 117 or confirm whether the related-report management information having the same combination is archived or not).

In response to the diagnostic report search request, the report searching part 14C firstly retrieves designation keywords and related keywords from the diagnostic report search request. Next, the report searching part 14C extracts related-report management information including a semantic unit composed of terms included in the retrieved designation keywords and related keywords, from the related-report management information archive 117. In this case, the report searching part 14C may be configured to extract related-report management information including a semantic unit composed of only terms included in the designated keywords and the related keywords, from the related-report management information archive 117. Alternatively, the report searching part 14C may be configured to extract related-report management information including a semantic unit including at least one of the terms included in the designation keywords and the related keywords, from the related-report management information archive 117.

Next, the report searching part 14C extracts a report ID from the extracted related-report management information. After extracting the report ID, the report searching part 14C extracts a diagnostic report including the report ID from the report storing part 12.

The diagnostic report extracted by the report searching part 14C is transmitted to the controller 15 as the search result and transmitted to the (transceiver 52 of the) search-result displaying part 5 as the source of request, via the controller 15 and the transceiver 16, as the result of search of the diagnostic report.

Accordingly, the diagnostic report searching apparatus according to the modified example 4 allows extraction of a diagnostic report including one or both of a designation keyword and a related keyword based on the related-report management information archived in the related-report management information archive. Thus, the report searching part 14C does not need to search all the diagnostic reports archived in the report storing part 12. This shortens a time to search for a diagnostic report, and it becomes possible to increase response when searching a diagnostic report.

Similarly to the report searching part 14 according to the first embodiment, the report searching part 14C may be configured to be capable of searching the report storing part 12 with a designation keyword and a related keyword as search keywords and extracting a diagnostic report including the designation keyword and the related keyword. For example, the report searching part 14C may be configured to be capable of, in response to an instruction by the operator, switching between extraction of a diagnostic report based on the aforementioned related-report management information and extraction of a diagnostic report by search with a designation keyword and a related keyword as search keywords. Moreover, the report searching part 14C may be configured to, in a case that a diagnostic report cannot be extracted based on related-report management information, perform search with a designation keyword and a related keyword as search keywords.

Further, similarly to the diagnostic report searching apparatus according to the modified example 2, the apparatus may be provided with the related-keyword library 116. Furthermore, similarly to the diagnostic report searching apparatus according to the modified example 3 or 3A, the apparatus may be configured so that the structuring processing part 110 extracts a diagnostic report from the report storing part 12 and structures the extracted diagnostic report.

Finally, in the apparatus configuration of the diagnostic report searching apparatus according to the first embodiment, the modified example 1, the modified example 2, the modified example 3 or the modified example 4, the configuration of each of the processing parts and the physical position of each of the processing parts are not limited.

For example, the report managing part 1 may be separated into a configuration relating to registration of a report and management of a related keyword and a configuration relating to search of a report. In this case, the configuration relating to registration of a report and management of a report has the report storing part 12, the report registering part 13, and the related-keyword managing part 11.

Moreover, the configuration relating to search of a report has the report searching part 14. The aforementioned configuration relating to registration of a report and management of a related keyword is equivalent to a diagnostic report search supporting apparatus.

Thus, according to the embodiments described above, the operator can display a list of terms having a close relation with a term inputted by him/her and narrow down desired diagnostic reports based on the terms. Therefore, a time to check the contents of diagnostic reports to search for desired diagnostic reports is reduced, and diagnostic reports having a close relation with a designation keyword can be searched out entirely. Moreover, since the terms having a close relation with the term inputted by him/her are presented, it becomes possible to easily consider another possibility of determination of interpretation entirely. Besides, since it is possible to check a relation of a typical diagnosed disease name with a finding or a relation of a typical finding with a diagnosed disease name, it becomes possible to use in education.

While certain embodiments have been described, these embodiments have been presented by way of example only, and are not intended to limit the scope of the inventions. Indeed, the novel methods and systems described herein may be embodied in a variety of other forms; furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. A diagnostic report search supporting apparatus, comprising:
   a memory configured to store a plurality of diagnostic reports in a retrievable manner;
   a report registering part configured to register a diagnostic report into the memory;
   a structuring processing part configured to, for each sentence written in the diagnostic report, extract terms from the sentence and classify the terms into predetermined types to structure the sentence written in the diagnostic report;
   a related-term analyzing part configured to generate a plurality of combinations, each composed of two or more terms, based on the plurality of terms extracted by the structuring processing part;
   a counting part configured to count an existence number of same combinations in the plurality of combinations, and extract combinations whose existence numbers are a predetermined number or more;
   a keyword inputting part configured to input a desired keyword; and
   a keyword extracting part configured to extract a combination that includes the inputted desired keyword from among the combinations extracted by the counting part, and extract a term other than the desired keyword from the extracted combination as a related keyword to obtain a search result for the inputted desired keyword;
   a report searching part configured to extract a diagnostic report including one or both of the desired keyword and the related keyword from the memory; and
   a related-report management information archive,
   wherein the counting part is configured to archive identification information of the diagnostic report as a source of extraction of the two or more terms composing the combination and the combination into the related-report management information archive; and
   the report searching part is configured to extract the identification information related with the combination including one or both of the desired keyword and the related keyword from the related-report management information archive and, based on the extracted identification information, extract the diagnostic report from the memory.

2. The diagnostic report search supporting apparatus according to claim 1, wherein:
   the structuring processing part includes a dictionary archive in which dictionary data including terms of finding fields and terms of diagnosed-disease-name fields of diagnostic reports is archived, and is configured to extract, from a diagnostic report, a term of a finding field and a term of a diagnosed-disease-name field that coincide with the terms included in the dictionary data; and
   the related-term analyzing part is configured to generate a combination of the term of the finding field and the term of the diagnosed-disease-name field having been extracted.

3. The diagnostic report search supporting apparatus according to claim 2, wherein:
   the dictionary data archived in the dictionary archive includes, as the term of the finding field, a term representing a region of a subject, a term representing an event occurring in the region, and a term representing certainty of the event;
   the structuring processing part is configured to extract the respective kinds of terms included in one sentence in a set; and
   the related-term analyzing part is configured to generate the combination based on the terms included in the set and the term of the diagnosed-disease-name field.

4. The diagnostic report search supporting apparatus according to claim 1, further comprising a displaying part configured to display a list of the related keyword extracted by the keyword extracting part.

5. The diagnostic report search supporting apparatus according to claim 1, wherein the keyword inputting part is configured to input a plurality of terms into the related-term analyzing part,
   wherein the related-term analyzing part is configured to further generate a combination composed of two or more terms based on the plurality of terms inputted by the keyword inputting part.

6. The diagnostic report search supporting apparatus according to claim 5, wherein the counting part is configured to separately extract the combinations generated based on the plurality of terms extracted from the sentence written in the diagnostic report and the combination generated based on the plurality of terms inputted by the keyword inputting part.

7. The diagnostic report search supporting apparatus according to claim 1, wherein the keyword extracting part is configured to, upon reception of a request to search for a keyword related to a term designated by an operator using a manipulation part, extract a combination including the term designated by the operator and extract the related keyword.

8. The diagnostic report search supporting apparatus according to claim 7, wherein when the report registering part archives a diagnostic report into the memory, the structuring processing part is configured to structure the sentence written in the diagnostic report, the related-term analyzing part is configured to generate the combinations, and the counting part is configured to count the combinations.

9. The diagnostic report search supporting apparatus according to claim 8, further comprising an archive in which combinations whose existence numbers are the predetermined number or more are archived, wherein
   after the counting part counts the combinations, the keyword extracting part is configured to cause the counting part to extract the combinations whose existence numbers are the predetermined number or more and archive the extracted combinations into the archive, and the keyword extracting part is configured to extract the combinations from the archive when receiving the request to search for a keyword.

10. The diagnostic report search supporting apparatus according to claim 7, wherein when the keyword extracting part receives the request to search for the keyword related with the term designated by the operator using the manipulation part, the structuring processing part is configured to structure a sentence written in a diagnostic report archived in the memory, the related-term analyzing part is configured to generate the combinations, and the counting part is configured to count the combinations.

* * * * *